United States Patent [19]

Chang

[11] Patent Number: 4,994,379

[45] Date of Patent: * Feb. 19, 1991

[54] MODIFIED SIGNAL PEPTIDES

[75] Inventor: Shing Chang, Hercules, Calif.

[73] Assignee: Cetus Corporation, Emeryville, Calif.

[*] Notice: The portion of the term of this patent subsequent to Dec. 8, 2004 has been disclaimed.

[21] Appl. No.: 407,701

[22] Filed: Aug. 22, 1989

Related U.S. Application Data

[63] Continuation of Ser. No. 583,472, Mar. 2, 1984, abandoned, which is a continuation-in-part of Ser. No. 473,820, Mar. 9, 1983, Pat. No. 4,711,844.

[51] Int. Cl.$^5$ .................. C12P 21/00; C12N 15/00; C12N 7/00; C07H 15/12
[52] U.S. Cl. .................. 435/69.1; 435/320.1; 435/69.52; 435/69.4; 435/69.8; 435/69.7; 435/172.3; 435/91; 435/252.3; 435/252.31
[58] Field of Search ............ 435/69.1, 69.4, 69.8, 435/69.52, 320, 69.7, 172.3, 91, 252.3, 252.31; 536/27; 935/47, 48, 29, 56, 60, 72, 73

[56] References Cited

PUBLICATIONS

McLaughlin et al., *Nucl. Acid Res.*, vol. 10(13) 1982, pp. 3705–3919, "Transcriptional Analyses of the *Bacillus licheniformis* penP Gene".
Nielsen et al., *J. Biol. Chem.*, vol. 257(8) Apr. 25, 1982, pp. 4490–4495, "Membrane-band Penicillinases in Gram-positive Bacteria".
Horowicz et al., *Nucleic Acids Rev.*, vol. 9(13) 1981, "Rapid and Efficient Cosmid Cloning".
Lai et al., *Proc. Natl. Acad. Sci.*, vol. 78(6), pp. 3506–3510, Jun. 1981, "*Bacillus licheniformis* Penicillinase Synthesized in *Escherichia coli* Contains Covalently Linked Fatty Acid and Glyceride".
Lin et al., *J. Bact.*, vol. 141(2) Feb. 1980, pp. 550–557, "Assembly of Outer Membrane Lipoprotein in *Escherichia coli* Mutant with a Signal Amino Acid Replacement within the Signal Sequence of Prolipoprotein".
Mezes et al., *J. Biol. Chem.*, vol. 258(18) Sep. 25, 1983, "Construction of penPΔI, *Bacillus licheniformis* 749/C β-Lactamase Lacking Site for Lipoprotein Modification".
Inouye et al, *EMBO J.* vol. 2(1) pp. 87–91, 1983, "Prolipoprotein Signal Peptidase of *Escherichia coli* Requires a Cysteine Residue at the Cleavage Site".
Nielsen et al., *Proc. Natl. Acad. Sci.*, vol. 78(6) pp. 3511–3515, Jun. 1981, "Lipoprotein Nature of *Bacillus licheniformis* Membrane Penicillinase".
Vlasuk et al., *J. Biol. Chem.*, vol. 258(11), Jun. 10, 1983, pp. 7141–7148, "Effects of the Complete Removal of Basic Amino Acid Residues from the Signal Peptide on Secretion of Lipoprotein in *Escherichia coli*".
Zweibel et al, *J. Bacteriology*, Jan. 1981, pp. 654–656, vol. 145(1), "Preferential Selection of Deletion Mutations of the Outer Membrane Lipoprotein Gene of *Escherichia coli* by Globomycin".

Primary Examiner—Robin L. Teskin
Attorney, Agent, or Firm—Gregory J. Giotta; Elliott L. Fineman; Albert P. Halluin

[57] ABSTRACT

The invention discloses modified signal peptides derived from wild-type signal peptides of the type that are capable of forming membrane-bound lipoproteins and methods for making such modified signal peptides and DNA sequences encoding them. Modified signal peptides of the invention and DNA sequences encoding them are useful for increasing the secretion of heterologous gene products produced by transformed host organisms. The invention further discloses a method for producing recombinant DNA sequences in vivo.

13 Claims, 6 Drawing Sheets

FIG. 5

| | 21 | 22 | 23 | 24 | 25 | 26 | 27 | 28 | 29 | 30 | 31 | 32 | 33 | 34 | | |
|---|---|---|---|---|---|---|---|---|---|---|---|---|---|---|---|---|
| pSYC310-2: | TGC | GTC | GCG | CTT | GCA | GGA | TGC | GCT | AAC | AAT | CAA | ACG | AAT | GCC | ① TCG | |
| | cys | val | ala | leu | ala | gly | cys | ala | asn | asn | gln | thr | asn | ala | ser | |
| pSYC660: | | | | | | | 27 TCC | | | | | | | | ① TCG | |
| | | | | | | | ser | | | | | | | | ser | |
| pSYC660A: | | | | | | | 27 GCT | | | | | | | | ① TCG | |
| | | | | | | | ala | | | | | | | | ser | |
| pSYC947: | | | | | | | 27 TCT | 28 CCT | | | | | | | ① TCG | |
| | | | | | | | ser | pro | | | | | | | ser | |
| pSYC947A: | | | | | | | 27 GCG | 28 CCT | | | | | | | ① TCG | |
| | | | | | | | ala | pro | | | | | | | ser | |
| pSYC957: | | | | 24 CCA | 25 GAT | 26 CTT | 27 GCA | 28 GGA | 29 TCC | 30 GCT | | | | | ① TCG | |
| | | | | pro | asp | leu | ala | gly | ser | ala | | | | | ser | |
| pSYC617: | | | 23 GCT | 24 AAC | 25 AAT | 26 CAA | 27 ACG | 28 AAT | 29 GCC | 30 TCG | 31 AAC | 32 AAT | 33 CAA | 34 ACG | 35 AAT | 36 GCC ① TCG |
| | | | ala | asn | asn | gln | thr | asn | ala | ser | asn | asn | gln | thr | asn | ala ser |

```
pSYC720:  23   24   25   26   27   28
          GCG  CTT  GCA  GGA  TCA  GCT
          ala  leu  ala  gly  ser  ala
                                        ①
                                        TTC
                                        phe  ①
pSYC852: ——— par ———                    TTC
pSYC970:       24   25   26   27   28   29   30
               CCA  GAT  CTT  GCA  GGA  TCA  GCT
               pro  asp  leu  ala  gly  ser  ala
                                                  ①
                                                  TTC
                                                  phe
pSYC744:                      27   28   29   30   31   32   33   34
                              TGC  GCT  AAC  AAT  CAA  ACG  AAT  GCC  TTC
                              cys  ala  asn  asn  gln  thr  asn  ala  phe
                                                                       ①
pSYC748:                      27                                       34
                              TCC                                      GCC  TTC
                              ser                                      ala  phe
pSYC728:                      27   28   29   30   31   32   33   34
                              TGC  GCT  AAC  AAT  CAA  ACG  AAT  GCA  GCT  TTC—
                              cys  ala  asn  asn  gln  thr  asn  ala  ala  phe
                                                                            ①
pSYC778:                      27   28                                       GCT  TTC—
                              TCT  CCT                                      ala  phe
                              ser  pro                                           ①
pSYC962:                      27   28                                       GCT  TTC—
                              TCT  CCT                                      ala  phe
                              ser  pro
```

FIG. 6

MODIFIED SIGNAL PEPTIDES

This application is a continuation of application Ser. No. 583,472, filed Mar. 2, 1984. which is a continuation-in-part of application Ser. No. 473,820, filed Mar. 9, 1983, now allowed U.S. Pat. No. 4,711,844.

TECHNICAL FIELD

This invention relates to molecular biology and, more particularly, to the art of recombinant DNA. Specifically, the invention relates to methods for producing modified signal peptides and to modified signal peptides useful for increasing the secretion of heterologous gene products produced by transformed hosts. The invention further relates to a method for producing recombinant DNA sequences in vivo.

BACKGROUND ART

Although protein synthesis occurs intracellularly, some proteins function outside the cell. These extra-cellular proteins are referred to as secreted proteins. Many of the secreted proteins are expressed initially inside the cell in a precursor or a pre-protein form. These pre-proteins contain an appended amino terminal extension called a signal or leader sequence (or signal peptide). The signal sequence plays an essential role in transporting the appended peptide into and/or through limiting cellular membranes.

Signal sequence encoding DNA can be included in recombinant expression vectors. The use of such vectors now makes it possible to transform compatible host organisms so they will produce heterologous gene products. The host organisms are often bacteria since bacteria can be grown with relative ease in chemically defined media. Growth of the organisms is rapid and high product yields are possible. When suitable host bacteria are transformed to produce desired gene products, such gene products are often easier to detect and purify if they are secreted into the periplasmic space or into the growth medium. Secretion of desired gene products into the medium avoids the necessity of breaking up the host organisms in order to recover the product. In addition, some heterologous gene products have a toxic effect on the host organisms. When such heterologous gene products are secreted rather than being allowed to accumulate within the host, they are less likely to interfere with normal cellular functions.

In some instances, the signal sequence is cleaved proteolytically during or after secretion to yield a mature protein product that is dissociated from the limiting cellular membranes through which it passed. In other instances, although the signal sequence is also cleaved, the mature protein remains bound to the cell membrane because of further modifications which lead to covalent attachments of lipid to the amino termini of the mature protein. *Escherichia coli* lipoproteins are an example of such membrane-bound proteins; *E. coli* betalactamase is an example of a protein that is dissociated from the membrane following cleavage of the signal sequence, and as a result the mature beta-lactamase is secreted into the *E. coli* periplasmic space. Such secreted proteins are called exoproteins. Other proteins, however, such as *Bacillus licheniformis* beta-lactamase, which herein is also referred to as penicillinase, can be processed into two different mature protein forms, one of which is a secreted exoprotein form, the other of which is a membrane-bound lipoprotein form. In the lipoprotein form of penicillinase, the first 26 of the 34 amino acids of the penicillinase signal sequence appear to function as the actual transport portion of the signal peptide. Some or all of the remaining 8 amino acids appear to be involved, along with some of the carboxy-terminal amino acids in the transport portion of the signal peptide, in the formation of the lipoprotein form.

Although not entirely understood, the mechanism by which mature protein (lipoprotein form) becomes bound to a cell membrane appears to involve the formation of a lipid bond at a site located near or within the signal peptide. Attachment of the lipid appears to anchor the protein into the cellular membrane. Specific amino acid sequences in the region of the junction of the signal sequences and the mature protein capable of forming membrane-bound forms are believed to function as recognition sites for the cellular agents involved in the chemical modifications leading to the formation of the membrane-bound lipoproteins. These specific chemical modifications are thought to include covalent bonding of fatty acids to the signal sequence moieties.

The usefulness of signal sequences capable of promoting lipoprotein formation would in some cases be improved if the recognition sequences could be modified in a way that would increase the amount of unbound exoprotein that is secreted into the periplasmic space or into the growth medium. Such a modified signal sequence could of course also lead to a decrease in the amount of the membranebound lipoprotein that is formed.

DISCLOSURE OF THE INVENTION

This invention seeks to improve the effectiveness of secretion by bacterial hosts of certain peptides they produce, either bacterial proteins, or, more usually, heterologous peptides synthesized by virtue of transformation with recombinant DNA sequences. It has been possible to alter the wild-type coding sequences for the signal peptides which are to be linked with these desired proteins to enhance the effectiveness of the signal in transporting these proteins through the cytoplasmic membrane into the medium (in the case of Gram positive bacteria) or into the periplasmic space and in some cases into the medium (in the case of Gram negative bacteria). Advantage is taken of wild-type signal sequences which are, in nature, capable of transporting cellular proteins to a membrane and of facilitating the binding of the attached protein to such membrane as a lipoprotein. By retaining the ability of the signal to transport the desired protein to the membrane, but interfering with its ability to facilitate membrane binding, the signal is made more effective in causing secretion.

Accordingly, in one aspect, the invention relates to a DNA sequence encoding an improved, novel, "exo-signal" peptide which has an amino acid sequence which includes an amino acid X in place of a cysteine residue of a corresponding wild-type signal peptide; wherein said wild-type signal peptide a) is capable of forming membrane bound lipoproteins, and b) contains a facilitating region which includes a single cysteine; wherein X will not function to form membrane bound lipoproteins; and wherein the cysteine replaced by X is that in the facilitating region of b).

The invention includes, in other aspects, DNA sequences encoding fused peptides comprising a desired protein operably linked to an exo-signal peptide, expression vectors capable of effecting the production of these fused peptides, to cells transformed with these vectos, and to the exosignal peptides and fused peptides produced by culturing the transformed cells.

The invention also relates to methods of improving secretion by using the coding sequences, vectors and transformed organisms of the invention, and to a novel method of modifying a DNA sequence through in vivo recombination.

BRIEF DESCRIPTION OF THE DRAWINGS

FIG. 5 shows the codon and amino acid sequences corresponding to vectors of the invention which contain the coding sequence for penP mature protein (large exopenicillinase) as the desired protein.

FIG. 6 shows the codon and amino acid sequences corresponding to vectors of the invention which contain the coding sequence for hGH mature protein as the desired protein.

MODES OF CARRYING OUT THE INVENTION

A. Definitions

Figure 1:
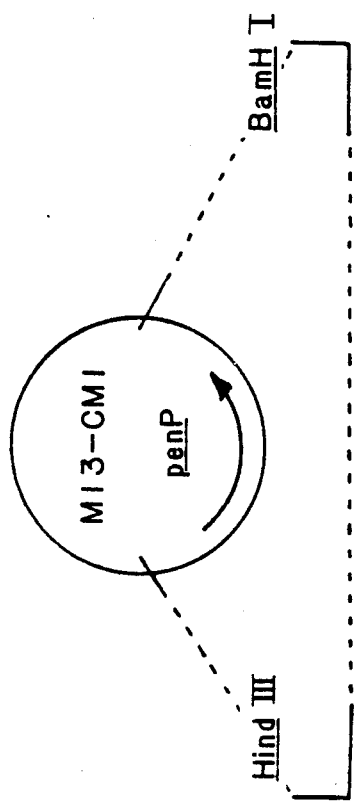
FIG. 1 is a codon diagram illustrating the construction of the cysteine$_{27}$ to serine$_{27}$ mutation.

As used herein, the terms signal peptide, leader peptide, signal sequence and leader sequence are used interchangeably. Such terms are meant to denote amino terminal protein extensions responsible for transport of the protein into or through cell membrane.

In general, such sequences are characterised by a hydrophilic, sometimes charged, N-terminal amino acid sequence, followed by a "hydrophobic core" of 10-25 mostly neutral and hydrophobic amino acids and, optionally, an additional carboxy terminal sequence linked to the protein to be secreted. A short series of amino acids proximal to the C-terminus of, and within the sequence of, the hydrophobic core appears to be involved in facilitating the binding of lipoprotein to the membrane. The cysteine residue which is replaced in the "exo-signal" peptides of the invention is in this "facilitating sequence"; other cysteine residues in the wild-type signal sequence need not be so replaced in the "exosignal" peptides of the invention.

Secretion of the desired protein requires a cleavage site adjacent its N-terminus. It is generally believed that such cleavage takes place following an alanine residue, and that, indeed, the presence of the alanine residue is required for cleavage. However, this is not proven, and any amino acid sequence which permits effective cleavage proximal the N-terminus of the desired protein is usable in the exo-signal peptides of the invention.

"Exo-signal peptide" (or exo-signal sequence) is a signal peptide capable of effecting the secretion of a polypeptide or protein which forms an extension from its carboxy terminus. Each of the exosignal peptides of the invention is related to a corresponding wild-type signal peptide in that another amino acid has been substituted for a cysteine residue of the wild-type sequence. The "corresponding wild-type" signal peptides which are useful in this invention are those which are found in bacterial systems to be capable of associating an operably linked polypeptide or protein to a membrane as a membrane bound lipoprotein. Exemplary of such corresponding wildtype signal peptides is the *B. licheniformis* penicillinase leader sequence.

It is understood that the wild-type sequences to which the exo-signal sequences of the invention correspond are subject to minor variation in length and amino acid composition due to species variation, mutation (intentional and spontaneous), errors in translation and the like. Thus, "wild-type signal sequence" is not necessarily limited to the precise sequences of amino acids published as determined for particular bacterial strains, bu includes any similar sequence which substantially retains the activity of the wildtype sequence.

As stated above, these wild-type sequences contain a "facilitating region" which appears to be associated with the integration of the appended peptide into the membrane. For example, in *B. licheniformis* penicillinase signal, a series of amino acids, Leu-Ala-Gly-Cys, is found at positions 23-27 of the signaled precursor, and the membrane bound protein resulting from the signaled precursor begins at the foregoing Cys (while the corresponding exoprotein begins at position 35). This region, immediately adjacent and partially including the membrane bound protein which results, appears to facilitate the binding to membrane. It is the cysteine of this region whose replacement is necessary to result in a protein of the invention.

Further, by "corresponding to" is meant substantially analogous, but not necessarily completely identical. The exo-signal peptides of the invention, each of which has an alternate amino acid residue in place of the appropriate cysteine of the "corresponding" wild-type signal peptide, exhibit substantial sequence homology with the wild-type signal, (except for the Cys residue), but may, for example, be slightly longer or shorter, or may have additional modifications, so long as an appropriate cleavage site for release of the desired protein is present.

The constructions illustrated herein show that additional modifications can be made to the exo-signal peptides of the invention which do not destroy the utility of these peptides in effecting secretion of a desired Protein. For example, such peptides may be modified by deletion of the amino acids analogous to amino acids 29-34 of the corresponding penP sequence; by insertion of a Pro-Asp dipeptide between the amino acids analogous to amino acids 23 and 24 of the corresponding penP leader; by insertion of an Ala preceding the N-terminus of the desired protein or by substitution of a Pro residue for the Ala residue at position 28 of the corresponding penP leader, or by combinations thereof.

As used herein, the term "penP" is meant to denote the prepenicillinase gene of *B. licheniformis* strain 749/C, or, where clear from the context, a relevant portion thereof. The nucleotide sequence of penP has been published by Kroyer, J., and Chang, S., *Gene* 15:343-347 (1981), and Neugebauer, K., Sprengel, R., and Schaller, H., *Nucleic Acids Research* 9:2577-2589 (1981).

As used herein, and where indicated by the context, the term fused peptide or fused protein is meant to denote polypeptide or protein comprising a signal sequence or a portion thereof joined to a desired protein sequence. Fused peptide and fused protein are used interchangeably. As used herein, the term desired protein is meant to denote a polypeptide or protein produced by a procaryotic host by virtue of its transformation with a recombinant vector comprising a DNA sequence coding for the polypeptide or protein. Such protein may be one otherwise ordinarily produced by this or another procaryotic organism or may be heterologous.

As used herein, the term "membrane binding" is meant to denote the anchoring on or anchoring into a membrane.

As used herein, "hGH" are meant to denote human growth hormone; "IL-2" means interleukin-2 from any source.

"Derivative plasmids" is meant to denote offspring produced during recombination. Derivative plasmids resulting from such recombinations will not necessarily be functionally equivalent to the parental plasmids used to form them.

"Operably linked" refers to juxtaposition of the sequences referred to in such a manner that their normal functions are maintained. Thus, promoters or control sequences operably linked to coding sequences effect transcription and translation of the codons; signal sequences operably linked to desired proteins effect the secretion or membrane association of the desired proteins. Exo-signal sequences operably linked to desired peptides effect the secretion of the desired peptides.

As used herein, "codon" means, interchangeably, (i) a triplet of ribonucleotides in an mRNA which is translated into an amino acid in a polypeptide or a code for initiation or termination of translation or (ii) a triplet of deoxyribonucleotides in a gene whose complementary triplet is transcribed into a triplet of ribonucleotides in an mRNA which, in turn, is translated into an amino acid in a polypeptide or a code for initiation or termination of translation. Thus, for example, 5'-TCC-3' and 5'-UCC-3' are both "codons") for serine, as the term "codon" is used herein.

As used herein, "nucleotide", "deoxynucleotide", and "deoxyribonucleotide" all mean deoxyribonucleotide.

dNTP or NTP means any of the deoxyribonucleotide triphosphates, i.e., ATP, GTP, CTP or TTP.

"bp" means base pair, and "kbp" means kilobase pairs.

"Polypeptide" means any peptide with two or more amino acids, including proteins. "Coding sequence" or "DNA coding sequence" means a DNA sequence encoding a polypeptide.

B. General Description and Preferred Embodiments

The methods of the present invention make use of techniques of genetic engineering and molecular cloning. General techniques of genetic engineering and molecular cloning are included in Maniatis, T., Fritsch, E. F., and Sambrook, J., *Molecular Cloning: A Laboratory Manual*, Cold Spring Harbor Laboratory (19821, and *Methods in Enzymology*, Volume 68, Recombinant DNA, (Wu, R., editor), Academic Press, New York, 1979.

Use of these techniques provides a means to produce modified (exo-signal) peptide sequences derived from wild-type signal peptide sequences of the type that are capable of forming membrane-bound lipoproteins. As used herein, derived from is meant to include mutated or synthetic signal sequences which correspond to wild-type signal sequences. The wild-type sequences include a facilitating region near the carboxy-terminal end of the hydrophobic core portion as discussed above. In this facilitating region is a single cysteine moiety, the presence of the cysteine being necessary for the formation of the membrane-bound lipoprotein. In DNA sequences of the invention coding for the exo-signal peptides, the codon for this cysteine is replaced with a codon for an amino acid other than cysteine that will not function to form membrane-bound lipoprotein.

The invention discloses such modified "exo-signal" peptides corresponding to wild-type signal sequences, which wild-type signal sequences are capable of forming membrane-bound lipoproteins. Such wild-type sequences include those sequences found in procaryotes in nature and the functional equivalents thereof. *B. licheniformis* penicillinase signal sequences, *E. coli* lipoprotein (lpp gene product) signal sequences, *Bacillus cereus* penicillinase 111 signal sequences, and *S. aureus* penicillinase signal sequences are examples of wild-type sequences capable of forming membrane-bound lipoproteins. *B. licheniformis* penicillinase signal sequences are especially preferred in practicing the invention for producing the exo-signal peptide sequences. The wild-type signal peptides capable of forming membranebound lipoproteins and corresponding to exo-signal peptides of the present invention are believed to include facilitating regions or sequences. For example, the amino acids Leu-Ala-Gly-Cys are contained in such a sequence in penP protein, and are located at amino acid positions 24–27. This facilitating sequence around the cysteine residue allows the cysteine to participate in the formation of the covalent bonds that will bind fatty acids to the peptide moiety. This same tetra-amino acid sequence comprised of Leu-Ala-Gly-Cys is found in several of the signal peptides capable of forming membrane-bound lipoproteins.

The exo-signal peptides of the invention are formed by substituting the codon for the cysteine in the facilitating amino acid sequence with a codon for an amino acid other than cysteine in the DNA coding sequence, said other amino acid being one that will not function to form membrane-bound lipoprotein. Preferred codons are those for amino acids having neutral side chains of less than 3 carbons. Especially preferred is substituting the codon encoding the amino acid cysteine with a codon for the amino acid serine. DNA nucleotide substitution can be accomplished using methods known to those skilled in the art. Such methods include the method for single nucleotide alteration disclosed in U.S. Pat. No. 4,351,901. A more preferred method for accomplishing the nucleotide substitution is the method of primer directed mutagenisis. See Zoller, M. J., and Smith, M., *Nucleic Acids Research*, 10:6487–6500 (1982). In utilizing the more preferred primer directed mutagenisis method, the DNA sequence coding for the amino acid sequence in the region of the signal peptide surrounding and including the cysteine to be substituted is determined, and based on this sequence a synthetic nucleotide fragment of approximately 10-25 nucleotides is synthesized using methods known to those skilled in the art. Such methods include the phosphotriester method of Narang, S. A., Hsiung, H. M., and Brousseau, R., in *Methods in Enzymology*, 68:90–98, (Wu, R., editor), Academic Press (1979); and more preferably the method of M. Matteucci and M. Caruthers, *J. Amer. Chem. Soc.*, 103, 3185-3191 (1981}. Most preferably the synthesis is carried out with an automated synthesizer, such as the Model Sam One synthesis automation machine made by Biosearch Inc. of San Rafael, California.

The synthetic nucleotide fragment complements one strand of the DNA coding sequence for the signal peptide in the area of the cysteine to be substituted and serves as a primer for synthesis of a full length coding sequence for the modified signal peptide. More specifically, in one embodiment when the preferred penP signal sequence is being utilized as the signal sequence to be modified, the synthetic DNA fragment will correspond to the codons for the 5 amino acids from positions 25 to 29, except that the middle nucleotide in the synthetic primer will have a mismatched nucleotide that does not complement the corresponding nucleotide in the penP template. When wild-type signal sequences other than penP are used, such as that of penicillinase of *S. aureus* (McLaughlin et al., *J. Biol. Chem.*, 256, 11283–11291 (1981), the synthetic primer will contain mismatched nucleotides that will not complement the wild-type nucleotides in the region of the cysteine codon to be modified in the DNA coding sequence for those signal sequences.

The DNA sequence for wild-type penP signal sequence contains the codon (TGC), which codes for the cysteine at amino acid position 27. When the modified penP signal sequence contains a serine at amino acid position 27, the synthetic fragment will contain a TCC sequence in the corresponding position and thus code for serine and not cysteine. In practicing the method of the invention, the wild-type signal sequence to be modified is isolated from an organism or plasmid containing it. The wild-type penP signal sequence can be isolated from a plasmid such as pOG2165 using appropriate restriction enzymes. Plasmid pOG2165 is described in European Patent Application Publication Number 0,036,259. More preferably, it is isolated from plasmid pSYC310-2. Following purification of the DNA sequence containing a coding sequence for the wild-type signal sequence, the fragment is ligated to the replicative form (RF) of a single-stranded DNA phage such as coliphage M13mp9. See Zoller and Smith (1982), supra, Viera, J., and Messing, J., *Gene*, 19:259–268 (1982), and Messing, J. and Viera, J., *Gene*, 19:269–276 (1982). M13mp9, and closely related M13mpB, are available from Bethesda Research Laboratories, Inc., Gaithersburg, Maryland. The recombinant of coliphage DNA carrying the gene for a wild-type signal sequence is transformed into a *E. coli* JM101 or *E. coli* JM103, which upon subsequent culturing yield phage with single stranded DNA. The single-stranded DNA is isolated. The synthetic nucleotide fragment carrying the mismatched nucleotide, which had been 5′-phosphorylated using ATP and T4 polynucleotide kinase (see Maniatis et al., (supra), p. 123) is annealed to the template single-stranded phage DNA carrying the wild-type penP leader sequence. The annealed synthetic fragment is then used as a primer to initiate the synthesis of the complementary strand DNA in vitro. Complementary (minus) strands are synthesized by primer extension reaction using Klenow fragment of *E. coli* DNA polymerase I on the phage DNA template. In the presence of T4 DNA ligase in this reaction, a fraction of the DNA molecules is converted to double-stranded, covalently-closed relaxed circles. These molecules are separated from the other molecules which either were incompletely extended by polymerase or failed to be ligated due to the incomplete kinase reaction of the primer. The molecules are separated by agarose gel electrophoresis, or alkaline sucrose gradient centrifugation (Zoller and Smith (1982), supra. Purified covalently closed double-stranded DNA is then used to transform competent *E. coli* cells, preferably *E. coli* JM103. Transformants containing phages carrying the gene coding for a protein with the modified signal sequences are identified and isolated. Confirmation that doublestranded phage DNA carry the intended mutation in the signal sequence can be obtained by analyzing for an added or a lost restriction endonuclease cleavage site due to the mutation, DNA sequencing of the region of the gene expected have been mutated, or DNA-oligonucleotide hybridization using, in radiolabeled form, the synthetic oligonucleotide primer used for the mutagenisis as the probe. See Zoller and Smith, (1982) supra. A fragment of the phage containing the gene with the cysteine to serine mutation in the signal sequence is removed, preferably by cleavage of the phage with restriction enzymes. Following purification, the fragment is cloned into a suitable cloning vector, replacing a fragment containing the wild-type gene, without the mutation in the signal sequence, that had previously been cloned into this plasmid.

Unless otherwise noted, all isolations of DNA fragments by "gel elution" were by eletroelution with acrylamide gels, using essentially the procedure in Maniatis et al. (1982), supra, at p. 164, but substituting acrylamide for agarose.

Unless otherwise noted, "T4 ligase" means T4 DNA ligase.

Unless otherwise noted, all transformations of *E. coli* strains are carried out by the method of Cohen et al., *Proc. Nat'l Acad. Sci.*, 69, 2110 (1973) and all transformations of *B. subtilis* strains by following procedures of Anagnostopoulus and Spizizen *J. Bacteriol.*, 81, (1961).

Unless otherwise noted, restriction enzymes and other enzymes referred to herein were obtained from New England Biolabs (Beverly, Massachusetts) or Bethesda Research Laboratories (Gaithersburg, Maryland) and used according to the supplier's specifications.

The exo-signal peptides produced according to the method of the invention will contain an amino acid X, i.e., an amino acid other than cysteine, in place of the cysteine contained within a facilitating region. Especially preferred is a modified *B. licheniformis* penicillinase (penP) signal sequence containing a serine at amino acid position 27 of the signal peptide sequence. The serine at amino acid position 27 replaces the cysteine found within the conserved facilitating Leu-Ala-Gly-Cys extending from amino acid positions 24–27 in the wild-type *B. licheniformis* penP signal sequence. Also preferred is a modified penP signal sequence containing an alanine at amino acid position 27 to replace the cysteine found at this location in the wild-type *B. licheniformis* penP signal sequence.

The invention further discloses a method for altering a DNA base sequence by heteroduplexing followed by in vivo recombination. Two parental plasmids having substantial structural homology, except for portions thereof, are converted from closed circular forms to open blunt-ended linear forms by digesting each with a restriction enzyme which cuts the treated plasmid at least about 20 bp distal to the cleavage site on the other plasmid, as measured from analogous loci and blunting with S1 nuclease. The blunt-ended, double-stranded linear DNA is separated and allowed to anneal and recircularize randomly to form heteroduplexes which may include single-stranded DNA sequence portions corresponding to different DNA sequence portions on the two parental plasmids, respectively. Because the enzymes used to cut the parental plasmids cut at offsets from analogous locations, heteroduplexes have extended sticky ends corresponding to these offsets, and can circularize. Homoduplexes do not have sticky ends and cannot circularize. These heteroduplexes are then introduced into transformable hosts and the transformable hosts are allowed to accomplish in vivo recombination of the DNA sequence portions of the recircularized heteroduplexes, thereby producing derivative plasmids containing recombinations of the different DNA sequence portions carried on the two parental plasmids. The recombined plasmids are then screened for the derivative plasmids carrying desired recombinations which are used to transform competent and susceptible host organisms.

In somewhat more detail, in practicing this aspect of the invention, a pair of parental plasmids is utilized. The parental plasmids will have substantial structural homology with one another but each will have a DNA sequence slightly different from the analogous positions in the other. For example, parental plasmid (A) might contain a sequence (y) which will code for a desired gene product. Parental plasmid (A') will have substantial sequence homology with parental plasmid (A) but will contain a different sequence (z) in the positions analogous to (y). The pair of parental plasmids, (A) and (A'), are each linearized with a restriction enzyme. The restriction sites are chosen to be at least 20 bp distant from analogous locations on the two plasmids. If the restriction enzyme digestion leaves single-stranded tails, the termini are made blunt with a single-strand specific nuclease, such as S1, or a repair reaction, such as that using *E. coli* DNA polymerase I Klenow fragment and required dNTP's, to prevent homoduplex circularization. Duplexed molecules are then formed by melting and annealing. Molecules referred to as homoduplex molecules will contain DNA strands only from parental plasmid (A) or from parental plasmid (A'). Heteroduplex molecules will contain a DNA strand from parental plasmid (A) as well as a DNA strand from parental plasmid (A') and will circularize because of the sticky ends created by the region between the two digestion sites. In their circularized form they are able to transform hosts efficiently. Homoduplex molecules do not transform hosts effeciently due to their inability to circularize; their blunt matching ends do not ligate. Unique sequences, such as (y) and (z), on each of the parental strands (the mismatched sequences) in the heteroduplexes can be selectively incorporated into or deleted from derivative plasmids as a result of the in vivo repair activities in transformed cells. These in vivo repair processes remove hanging tails, fill in gaps, remove loops, and correct mismatches. In addition, mispaired sequences due to allelic differences between the parental plasmids can be incorporated into the derivative plasmids as well.

This method of the present invention permits the generation of new recombinant sequences in plasmids in vivo without relying solely on the direct ligation of restriction fragments in vitro. In a preferred form of this aspect of the invention, parental plasmids are selected which contain sufficient sequence homology to allow single strands of DNA from each plasmid to anneal with single strands of DNA from the other plasmid. The parental plasmids will each contain unique sequences that will not be found on the other parental plasmid. The parental plasmids DNA will be isolated using techniques known to those skilled in the art. Such techniques include cesium chloride gradients and the small scale method of Ish-Horowicz, D., and Burke, J. R., *Nucleic Acids Research* 9:2989-2998 (1981). Each parental plasmid is cleaved with an appropriate restriction enzyme. Use of such enzymes is well known to those skilled in the art. Such enzymes can be purchased from sources such as New England Biolabs or Bethesda Research Laboratories and used according to the supplier's specifications.

To prepare the heteroduplexes, linearized plasmid DNA, if it contains single-stranded protruding ends, is first treated with an enzyme such as S1 nuclease in an appropriate buffer in order to digest the single-stranded tails that can result from restriction enzyme digestion to thus prevent recircularization of homoduplexes. Following treatment with the S1 nuclease, the plasmid DNA is extracted and precipitated. The plasmid DNA is then resuspended in an appropriate annealing buffer. A solution containing both parental DNA's is heated for an amount of time sufficient to separate the strands of DNA. The heated solution is then allowed to gradually cool at room temperature to permit the separated DNA single strands to anneal with one another and circularize. Techniques other than heating and cooling, e.g., alkaline denaturation followed by return of pH to near neutrality, can be used for strand separation and annealing. After annealing and circularization, the DNA is then used to transform a transformable host. Only heteroduplexes which circularize will transform with significant frequency. The hanging tails (which result if there are non homologous extensions of the sticky ends) and single-stranded gaps in the heteroduplex molecules, as illustrated will be removed or repaired by transformed cells in vivo. This in vivo recombination will result in the formation of new recombinant derivative plasmids. Mispaired sequences due to allelic differences between the parental plasmids can also be incorporated with high frequency into the recombinant derivative plasmids by means of the heteroduplex transformation procedure of the present invention. Clones carrying the desired recombinant derivative plasmids are isolated. The recombinant derivative plasmids are isolated and used to transform transformable hosts.

Specific embodiments of the present invention are outlined in the following examples. Such examples are for illustrative purposes only and are not intended to limit the scope of the claims in any way.

EXAMPLE I

Construction of a Deletion Mutation at Amino Acid Positions 23 Through 27 in the *B. licheniformis* 749/C Penicillinase Signal Sequence.

The DNA sequence of the *B. licheniformis* penicillinase (penP) gene is known. See Kroyer, J., and Chang, S., *Gene* 15:343-347 (1981) and Neugebauer, K., Sprengel, R., and Schaller, H., *Nucleic Acids Research* 9:2577-2589 (1981). The DNA sequence data reveals that there are only two HhaI (GCGC) recognition sequences in the penP gene, at the codon for the 23rd amino acid (together with the first nucleotide in the codon for the 24th) and at the last two nucleotides in the codon for the 27th amino acid together with the first two nucleotides in the codon for the 28th. These two HhaI sites in the penP gene flank the Leu-Ala-Gly-Cys sequence at positions 24-27, where the Cys at positon 27 is modified at its sulfur with glyceride in the membrane bound form of the enzyme. This same Leu-Ala-Gly-Cys sequence, with the Cys modified with glyceride in membrane bound protein, is found in the signal peptides of several lipoproteins. The penicillinase of *S. aureus* PC1 has a similar Leu-Ser-Ala-Cys sequence, with Cys glyeridemodified in membrane bound form. See Nielsen and Lampen, *J. Biol. Chem.*, 257, 4490–4495 (1982).

Without knowing whether cells expressing a mutated penP gene containing the deletion covering this sequence would be viable, it was decided to initially generate the deletion mutation in a promoterless penP gene. This was made possible by using a plasmid designated plasmid pSYC423 which replicates in both *E. coli* and *B. subtilis* cells. The construction of pSYC423 from pSYC310-2 is described in McLaughlin et al., *Nucl. Acids Research*, 10, 3905–3918 (1982). Plasmid pSYC423 carries the complete coding sequence of *B. licheniformis* penP, but lacks its promoter. The penP sequence on plasmid pSYC423 is carried on a fragment flanked by EcoRI and BamHI sites. This plasmid, pSYC423, which contains many other HhaI sites outside of the EcoRI and BamHI bounded fragment, was first digested with HhaI enzyme, and the 3' protruding termini were then made blunt using the Klenow fragment from *E. coli* DNA polymerase I in the presence of the four deoxyribonucleotide triphosphates. Such methods are well known to those skilled in the art and can be found in such references as Maniatis, T., Fritsch, E. F., and Sambrook, J., *Molecular Cloning: A Laboratory Manual*, Cold Spring Harbor Laboratory, 1982. The blunt-ended HhaI fragments from plasmid pSYC423 were further digested with EcoRI and BamHI enzymes. Such enzymes were obtained from New England Biolabs (Beverly, Massachusetts) and were used according to the manufacturer's instructions. The EcoRI-HhaI fragment containing the 5' portion (337 nucleotides) of penP gene was purified by elution from acrylamide gels, following the procedure in Maniatis et al., (1982), supra, pp. 163-164 but using acrylamide in place of agarose. The HhaI-BamHI fragment (1kb) was purified by gel elution in the same manner. In a separate experiment, the large EcoRI to BamHI fragment on pSYC423 was also purified and ligated to these two penP derived fragments. The plasmid that resulted, designated plasmid pSYC562, contains a deletion covering the coding sequence for the AlaLeu-Ala-Gly-Cys (positions 23-27 on the wild-type *B. licheniformis* penP gene). Because there is also an Ala at position 28 in the wildtype sequence, this deletion can be considered the same as a deletion from positons 24-28. The remaining portion of pSYC562 is the same as that on plasmid pSYC423. Taking advantage of a nearby PstI site located 27 nucleotides upstream from the deletion, plasmid pSYC562 was digested with PstI, end-labeled and then its sequence was analyzed. See Gilbert, W., and Maxam, A., in *Methods in Enzymology* 65:499–560 (Grossman, L., and Moldave, K. J., editors) Academic Press (1980). The results confirmed that the sequence contained a deletion of nucleotides coding for amino acid residues from positions 23 through 27. This mutation is termed penP delta 2428.

In order to study the phenotype of the penP delta 2428 mutation, a wild-type penP promoter was added back to plasmid pSYC562. The 313 base pair (bp) EcoRI to PstI fragment containing the promoter and partial coding sequence, preceding the delta 2428 mutation, of penP was purified from plasmid pSYC310-2 (the parent of pSYC423). Plasmid pSYC310-2 is described by McLaughlin, J. R., Chang, S-Y., and Chang, S., *Nucleic Acids Research* 10:3905–3919 (1982). The fragment was then ligated with EcoRI- and PstI- digested DNA of plasmid pSYC562 in place of the small EcoRI to PstI fragment. *E. coli* transformants resistant to ampicillin were selected and a representative plasmid, pSYC617, was studied further. Based on analysis of fragmentation patterns using various endonucleases, plasmid pSYC617 was found to be identical to plasmid pSYC310-2 except for the presence of the 15 base pair deletion in penP delta 2428 as expected from the fragment switching experiment. A part of the penP delta 2428 gene on pSYC617 is illustrated in FIG. 5.

When plasmid pSYC617 was used to transform competent cells of *E. coli* CS412 or *E. coli* K-12/MM294 nearly all of the mature penicillinase remained intracellular or bound to the cytoplasmic membrane. Only very low levels of exopenicillinase were detected in the periplasmic space (i.e. released by osmotic shock). Thus it was concluded that deletion of the conserved sequence containing the cysteine at amino acid position 27 of the *B. licheniformis* signal sequence interferes with the production of exoenzyme. Similar results were obtained with *B. subtilis* BD224 transformed with pSYC617. See Example XIII.

EXAMPLE II

Construction of a Cysteine to Serine Mutation at Amino Acid Position 27 in the *B. licheniformis* Penicillinase Signal Sequence and Plasmid pSYC660 Carrying the penP $S_{27}$ Gene.

*B licheniformis* penicillinase (penP) gene has been sequenced. See Kroyer, J., and Chang, S., (1981), supra, and Neugebauer, K., et al. (1981), supra. The signal sequence contains the codon TGC which codes for a cysteine at amino acid position 27. The cysteine residue at position 27 is modified as part of a sequence of events leading to formation of the membrane-bound lipoprotein form of penicillinase. See Nielsen, J. B. K., Caulfield, M. P., and Lampen, J. O., *Proceedings National Academy of Sciences*, (USA) 78:3511–3515 (1981), and Lai, J. S., Sarvas, M., Brammar, W. J., Neugebauer, K., and Wu, H. C., *Proceedings National Academy Science*, (USA) 78:3506–3510 (1981). To specifically alter this biosynthetic pathway, and shunt more of the protein to the exoform secreted from the cell (in the case of Gram positive bacteria such as *B. subtilis*) or into the periplasmic space (in the case of Gram negative bacteria such as *E. coli*), it is necessary to mutate the sequence in the penicillinase signal sequence gene coding for cysteine at this position.

Because of its simplicity and efficiency, the method of primer-directed mutagenesis (see Zoller, M. J., and Smith, M., *Nucleic Acids Research* 10:6487–6500 (1982)) was used for the construction of the cysteine to serine mutation. A DNA fragment containing wild-type penicillinase (penP) gene sequence was isolated. Specifically the DNA fragment located between the HindIII and BamHI sites was excised from plasmid pSYC310-2. See McLaughlin, et al. (1982), supra. Plasmid pSYC310-2 is a bifunctional plasmid capable of replicating in both *B. subtilis* and *E. coli*. It carries the wild-type penP gene from *B. licheniformis* 749/C on the HindIII-BamHI fragment. Those skilled in the art will realize that the wild-type penP gene could have been excised from other engineered recombinant plasmids that carry it. One such plasmid is *B. subtilis* plasmid pOG2165. The excised HindIIIBamHI DNA fragment from pSYC310-2 was purified by acrylamide gel elution and then ligated to Replicative Form (RF) DNA of coliphage M13mp9. See Viera, J., and Messing, J., *Gene*

19:259–268 (1982) and Messing, J., and Viera, J., *Gene* 19:269–276 (1982).

Specifically the purified HindIII-BamHI fragment from pSYC310-2 was ligated to M13mp9, obtained from Bethesda Research Laboratories, Inc., P.O. Box 577, Gaithersburg, MD., that had previously been digested with restriction endonucleases HindIII and BamHI. The double-stranded phage DNA was transformed into *E. coli* JM103, and the cells were cultured. A clone transformed with recombinant phage carrying the penP gene, i.e. recombinant phage M13CM1, was identified and single-stranded phage DNA was prepared from this clone. The methods used are described in Zoller, M. J., and Smith, M., *Nucleic Acids Research* 10:6487–6500 (1982).

A 15-nucleotide synthetic fragment 5'-GTTAGC-GGATCCTGC-3', made by the phosphotriester method of Narang, S. A., Hsiung. H. M., and Brousseau, R., in *Methods in Enzymology* 68:90–97 (R. Wu, editor) Academic Press (1979), was first phosphorylated at the 5'-end with ATP and T4 polynucleotide kinase and then employed as a primer to initiate the synthesis of the complementary strand in vitro after the 5'-phosphorylated primer had been annealed to the template M13-CM1 DNA. The primer was extended using DNA polymerase I Klenow fragment with all four dNTP's in the presence of T4 ligase. This primer complements the anti-sense strand of the penP signal sequence gene segment corresponding to the codons for the five amino acids from positions 25 to 29, except that the middle nucleotide in the synthetic primer is a mismatched nucleotide, that does not complement the corresponding nucleotide, G, in the wild-type penP gene template. Incorporation of the mismatched sequence into the penP gene causes conversion of the cysteine (TGC codon) to serine (TCC codon) at position 27. FIG. 1 illustrates the process of making the $Cys_{27}$ to $Ser_{27}$ mutation.

The alteration on the encoded peptide is essentially a conversion of the —SH group on the $cysteine_{27}$ to the —OH group of the $serine_{27}$. At the nucleotide level, a mutant gains a BamHI site (GGATCC) and loses the HhaI (GCGC) at the mutation locus. The presence of a new BamHI site was the phenotype used to identify the mutants carrying the "G to C" nucleotide mutation.

In constructing the cysteine to serine mutation, complementary (minus) strands were synthesized by primer-extension reaction using Klenow fragment of *E. coli* DNA polymerase I on the M13-CM1 phage DNA template. See Zoller, M. J., and Smith, M., *Nucleic Acids Research* 10:6487–6500 1982}. In the presence of T4-DNA ligase in this reaction, a fraction of the DNA molecules was converted to double-stranded, covalently-closed relaxed circles. These molecules were separated from other molecules, which either were incompletely extended by polymerase or failed to be ligated due to the incomplete kinase reaction of the primer. Separation was accomplished by agarose gel electrophoresis. This was carried out by applying the reaction mixture on a 0.8% agarose gel in the presence of 2 micrograms/ml of ethidium bromide. The band containing covalently closed circular DNA was excised and DNA recovered.

Purified covalently closed double-stranded DNA was used to transform competent cells of *E. coli* JM103 using standard transformation procedures for M13 phage DNA. JM103 cells were obtained from Bethesda Research Laboratories, Inc., P.O. Box 577, Gaithersburg, MD. Also see generally, Viera, J., and Messing, M., *Gene* 19:259–268 (1982) and Messing, J., and Viera, J., *Gene* 19:269–276 (1982). A total of 36 phage plaques were isolated and RF DNAs from the phageproducing cells were analyzed using the quick plasmid screening method of Ish-Horowicz and Burke. See Ish-Horowicz, D. I., and Burke, J. F., *Nucleic Acids Research* 9:2989–2998 (19811. Upon digestion with BamHI restriction endonuclease, one of the 36 DNA preparations (designated $M13penPS_{27}$) yielded two fragments on agarose gel following electrophoresis, indicating that the "G to C" mutation had been incorporated into the gene sequence of that clone ($M13penPS_{27}$). The rest of the preparations showed a single cleavage by BamHI endonuclease indicating that the parental M13-CM1 DNA had not been mutated at this locus. Further analysis of the DNA from the mutant, $M13penPS_{27}$, using HhaI and BamHI endonucleases, showed the expected sequence alterations. Direct sequence analysis of this mutation further confirmed the sequence change.

The cysteine to serine mutation in $M13penPS_{27}$ is located between the PstI and the BglII sites in the penP gene. See McLaughlin, et al. (1982), supra for the location of these sites. This restriction DNA fragment was isolated from RF DNA of $M13penPS_{27}$. This "mutant" restriction fragment could be cloned into any penP-containing plasmid, such as bifunctional plasmids pOG2165 or pSYC310-2, in place of the corresponding fragment of wild-type penP sequence.

When the "mutant" PstI to BgJII fragment was isolated from RF DNA of $M13penPS_{27}$ and cloned into plasmid pSYC310-2, using standard techniques, in place of the corresponding PstI-BglII fragment in the wild-type sequence, a plasmid designated as pSYC660 resulted.

Plasmid pSYC660 contains the gene $penPS_{27}$, which has the cysteine to serine mutation at amino acid position 27 of the penP signal sequence, as shown in FIG. 5.

EXAMPLE III

Construction of a Cysteine to Alanine Mutation at Amino Acid Position Number 27 in the *B. licheniformis* Penicillinase Signal Sequence and Plasmid pSYC660A Carrying the $penPA_{27}$ Gene.

Following the procedures outlined in Example II, it is possible to create a cysteine to alanine mutation at amino acid position 27. The wild-type penP sequence contains the codon TGC which codes for the cysteine at amino acid position 27. The $serine_{27}$ modified signal peptide coding sequence contains the codon TCC which codes for the serine at amino acid position 27. By converting the TCC serine codon in $penPS_{27}$ to a GCT codon, a codon is created which codes for alanine.

The DNA sequence encoding $serine_{27}$-modified penP signal sequence is located on $M13penPS_{27}$ phage. See Example II, supra. A synthetic primer is synthesized having the sequence 5'TGTTAGCAGCTCCTGCAA-3'. The preparation of this synthetic primer is carried out by the method of Matteucci and Caruthers (1981), supra, applied on an automated oligonucleotide synthesizer (Model Sam One from Biosearch Inc., San Rafael, Calif.). The primer is used to initiate the synthesis of the complementary strand in vitro after the primer is 5'-phosphorylated and annealed to the template $M13penPS_{27}$ DNA. This primer complements the anti-sense strand of the modified ($ser_{27}$) signal sequence gene segment corresponding to the codons for the five amino acids from positions 25 to 29, except that the nucleotide at the 10th position from the 5'-end and the A at the 8th position from the 5'-end in the synthetic primer are mismatched nucleotides that do not complement the corresponding nucleotides in the penPS$_{27}$ gene template. Incorporation of the mismatched sequence into the penPS$_{27}$ gene causes conversion of the serine (TCC coden) to alanine (GCT codon) at position 27, resulting in a mutant gene called penPA27 in phage M13penPA27. Phage M13penPA27 is identified by the new AluI restriction site (AGCT) created and the BamHI site eliminated by the mutation. Replacing the PstI-BglII fragment of pSYC310-2 with the PstI-BglII fragment of the penPA27 gene results in plasmid pSYC660A, a part of the penPA$_{27}$ gene of which is shown in FIG. 5.

A higher percentage of penicillinase expressed from penPA$_{27}$ gene on pSYC660A would be secreted, in both *E. coli* and *B. subtilis*, then the percentage of penicillinase expressed from penP on pSYC310-2 in *E. coli* and *B. subtilis*, respectively.

A polypeptide fused behind an alanine downstream from the Ala-27 in the signal peptide provided by penPA$_{27}$ would be secreted with higher efficiency than the same polypeptide behind the alanine at position 34 in the wild-type signal peptide provided by penP.

EXAMPLE IV

Construction of a Series of Plasmids Having Convenient Restriction Sites Flanking the *B. licheniformis* Penicillinase penP Promoter and Signal Peptide-encoding DNA Sequences, Plasmid pDH5508.

The penicillinase penP gene from *B. licheniformis* has been sequenced. The sequence data revealed a 446 base pair HpaII fragment (see Kroyer, J., and Chang, S., (1981) supra, and Gray, O., and Chang, S., *Journal Bacteriology* 145:422–428 (1981), comprising the penP promoter and the coding sequence for the first 72 amino acids, including the 34 of the signal peptide.

There is an AvaI site in the penP gene (CTCGGG, see Kroyer, J., and Chang, S., (1981), supra. There is also an AvaI site in pBR322 at position 1425 (see Sutcliffe, J. G., *Cold Spring Harbor Symposium Quantitative Biology* 43:77–90 (1979)). Joining of the HpaII-AvaI fragment originating from penP (on, e.g., pSYC310-2, pOG2165 or pTB2 (Kroyer and Chang (1981), supra) and the large ClaIAvaI fragment originating from pBR322, transforming *E. coli* K-12/CS412 with the resulting plasmids, and selecting for ampicillin-resistant transformants, resulted in construction of a plasmid designated pOG2254.

Figure 2:
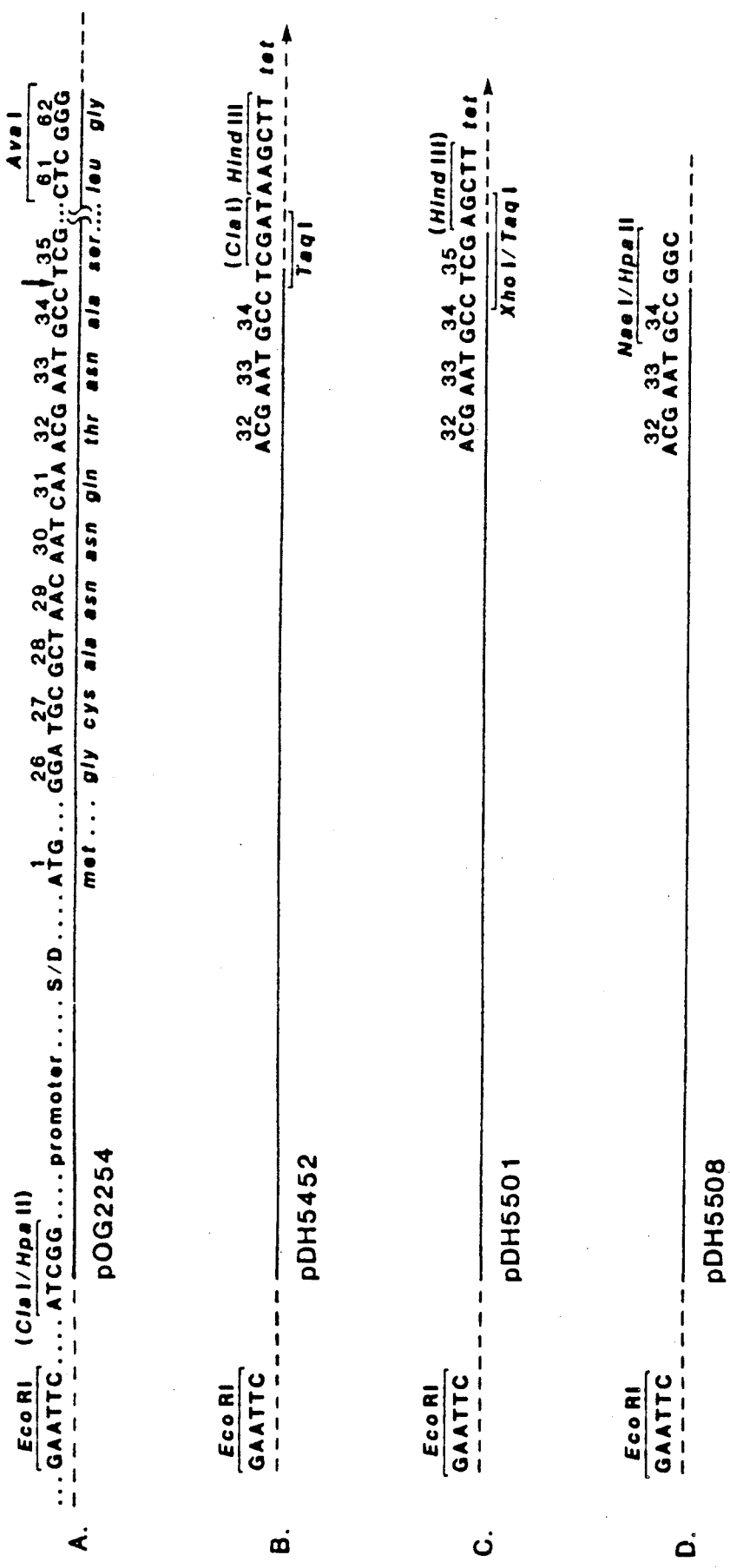
FIG. 2 is a nucleotide diagram illustrating a family of plasmids having convenient restriction enzyme sites flanking the penP promoter and signal sequence.

As illustrated in FIG. 2 plasmid pOG2254 contains sequences derived from penP gene flanked by the HpaII site and the AvaI site. The rest of the sequence in pOG2254, which includes the region from the AvaI site to the ClaI site, was derived from pBR322. Plasmid pOG2254 was linearized at the single AvaI site. The linearized DNA was treated with ExoIII enzyme for various lengths of time under the conditions specified by Guo, L. H., and Wu, R., *Nucleic Acids Research*, 10:2065–2084, (1982). ExoIII enzyme converts the terminal regions of double-stranded DNA to single-stranded termini. Samples were removed from the reaction mixture, and the ExoIII nuclease activity quenched, at different times; then the samples were pooled together. These DNA preparations were then treated with single-strand-specific nuclease S1 (obtained from Bethesda Research Laboratories, Inc. and used according to supplier's specifications). The S1 nuclease treatment specifically removes single-stranded DNA from the termini, thus generating flush-ended molecules.

DNA treated with ExoIII and S1 nuclease was then digested with EcoRI enzyme. The EcoRI site in the pOG2254 plasmid is located 5' to the penP promoter. Digestion with EcoRI releases a small fragment from these ExoIII and S1 treated DNA fragments, which contain the promoter of the penicillinase gene as well as various lengths of the amino terminal coding region of the penicillinase gene. These DNA fragments were fractionated on a gel. DNA fragments of approximately 300–400 base pairs were eluted from the gel and used for cloning experiments.

Each of these short, approximately 300–400 bp, DNA fragments has an EcoRI generated terminus on one side and a blunt-ended terminus on the other side. In order to clone these DNA fragments, plasmid pBR322 was digested with ClaI enzyme (position 23, which is located in the tetracycline-resistant gene promoter region, see Sutcliffe, J. G., *Cold Spring Harbor Symposium Quantitative Biology* 43:77–90 (1979)). The ClaI termini were then repaired with *E. coli* DNA polymerase I Klenow fragment. This treated DNA was then digested with EcoRI which generated a large fragment containing an EcoRI terminus and a bluntended terminus. This large fragment from pBR322 was purified from gel and mixed with the approximately 300-400 bp small fragments derived from penicillinase gene originated from pOG2254 as described above. The DNA's were ligated and then used to transform *E. coli* K-12/CS412. Transformants resistant to tetracycline were selected on plates; the recombinant plasmids they harbor were isolated and characterized by digestion with EcoRI and HindIII enzymes which revealed that they have inserts derived from the penicillinase gene in the range of 300–400 base pairs as expected.

Several plasmid DNA's were prepared from different clones and the nucleotide sequences at the junction regions between penP and pBR322 sequences were analyzed using the Maxam and Gilbert method. See Gilbert, W., and Maxam, H., in *Methods in Enzymology* 65:499–560 (Grossman, L., and Moldave, K. J., editors) Academic Press (1980). One of the plasmids, designated pDH5452, had the sequence such that the ExoIII and S1 nuclease generated deletions up to nucletode T corresponding to the TCG codon for the 35th amino acid of penP, which is Ser and is the N-terminal amino acid of the large exo form of the protein. The carboxy terminal amino acid of the signal sequence in wild-type penicillinase is Ala at position 34. This T was joined by ligation to the repaired ClaI site, originated from pBR322, having the sequence CGA. The junction sequence TCGA corresponds to the recognition sequence of restriction enzyme TaqI. Plasmid pDH5452 is illustrated in FIG. 2. Digestion with TaqI restriction enzyme generates CG protruding ends. Plasmid pDH5452 DNA was digested with TaqI enzyme and the 5' protruding-ends were filled in with DNA polymerase I Klenow fragment, dCTP and dGTP, using standard conditions, and then digested again with EcoRI enzyme. The fragment between EcoRI to repaired TaqI, which contains the promoter and the signal sequence of penP, was purified from this preparation by elution from gel and cloned into pBR322. The vector pBR322 DNA had been digested with HindIII enzyme and then repaired with DNA polymerase I Klenow fragment and the dNTP's under standard conditions. Following digestion with EcoRI, this pBR322 fragment was ligated to the preferred penP fragment from pDH5452 and transformed into *E. coli* K-12/CS412. One transformant, phenotypically resistant to ampicillin and tetracycline was isolated. Plasmid DNA from this transformant was prepared and analyzed. This plasmid is designated pDH5501. The repaired TaqI site was ligated to the repaired HindIII site and the new junction sequence, has the following sequencer CTCGAG. Within this sequence, CTCG was derived from pDH5452 and the AG residues were derived from repaired HindIII site of pBR322. This hexanucleotide sequence CTCGAG is recognized by restriction enzyme XhoI and the central four nucleotide TCGA is recognized by restriction enzyme TaqI. Plasmid pDH5501 is illustrated in FIG. 2.

To create additional restriction enzyme recognition sequences at the end of the penP signal sequence, plasmid pDH5508 was constructed. To generate this plasmid, plasmid DNA from pDH5501 was digested with NaeI enzyme which recognizes sequences in the region derived from pBR322 at four locations: 403, 770, 930, and 1284 (see Sutcliffe, J. G., *Cold Spring Harbor Symposium Quantitative Biology* 43:77–90 (1979)). NaeI recognizes sequence GCCGGC. Digestion with the enzyme leaves a blunt-ended sequences GCC-3' and 5'-GGC. NaeI digested pDH5501 DNA was further digested with XhoI enzyme. This was then treated with single-strand-specific nuclease S1 which generates blunt-ended fragments at the XhoI site bY removing protruding ends. This leaves the sequence GCC corresponding to nucleotode sequence for the 34th amino acids in the penP signal sequence. After ligation of NaeI, XhoI, S1 nuclease-treated DNA (at 10 micrograms/ml concentration of DNA) with T4 ligase, the resulting plasmid was used for transformation of *E. coli* K-12/CS412. An ampicillin-resistant tetracycline-sensitive transformant was obtained which harbors a plasmid designated pDH5508. Restriction analysis of pDH5508 showed that it has two NaeI sites, the downstream (clock-wise from the EcoRI site) one corresponding to the NaeI site located originally in pBR322 at position 1284. The upstream NaeI site corresponds to the junction sequence generated by S1 treated XhoI site which was ligated to the NaeI site originally located in pBR322 at position 930. The sequence located between the unique EcoRI site on pDH5508 and the first NaeI site downstream from it is the sequence derived from pDH5501 which contains penP promoter and the signal sequence of penicillinase. The NaeI site has the sequence GCCGGC, which can be cut both by NaeI enzyme and by HpaII enzymes. Plasmid pDH5508 is illustrated in FIG. 2.

Therefore, a series of plasmids was constructed, each of which has convenient restriction sites flanking the penP promoter and signal sequence. Plasmid pDH5452 has a TaqI restriction site, as well as a HindIII restriction site following the coding sequence of the signal peptide. Plasmid pDH5501 has an XhoI site and a TaqI site following the signal sequence, and plasmid pDH5508 has an NaeI site and a HpaII site following the signal sequence of penicillinase. See FIG. 2.

EXAMPLE V

Cloning of Human Growth Hormone (hGH) cDNA and Construction of Plasmid pSYC709.

Human pituitary glands were used as the source for the human growth hormone mRNA. The method used to isolate mRNA is the method described by Maniatis, T., Fritsch, E. F., and Sambrook, J., in Chapter 6 of *Molecular Cloning: A Laboratory Manual*, Cold Spring Harbor Laboratory (1982). The cDNA was made according to the published procedure and cloned into plasmid pBR322 using the methods outlined in Chapter 7 of Maniatis, T., Fritsch, E. F., and Sambrook, J., *Molecular Cloning: A Laboratory Manual*, Cold Spring Harbor Laboratory (1982). The pBR322 plasmid DNA was then digested with PstI enzyme. Terminal transferase was then used in the presence of dGTP to tail this vector DNA. The GTP-tailed DNA was annealed to doublestranded cDNA which had been tailed with dCTP. The annealed DNA was used to transform *E. coli* K-12/MM294. One tetracycline-resistant and ampicillin-sensitive transformant was identified (designated clone 20C4) which carries the hGH cDNA sequence in a plasmid (designated p20C4). The plasmid, p20C4, contains an hGH gene insert which can be digested with restriction enzymes BamHI and SmaI. These two enzymes generate a fragment of 688 base pairs which is the same as part of the fragment published by Martial, J. A., Hallewell, R. A., Baxter, J. D., and Goodman, H. M., *Science* 205:602–607, (1979). Since internal restriction sites, e.g. PstI, PvuII, were found that also match sites published by Martial, J. A., Hallewell, R.A., Baxter, J. D., and Goodman, H. M., *Science* 205:602–607, (1979), it was concluded that 20C4 carries cDNA coding for human growth hormone on p20C4.

Plasmids were isolated from clone 20C4. The plasmid DNA was digested with BamHI enzyme which cuts into the plasmid at two locations. One BamHI site cuts into the tetracycline (tet) gene in the pBR322 derived sequence and the other cuts into the cDNA sequence. The digested DNA was mixed with a synthetic oligoneuclotide prepared by the phosphotriester method of Narang et al. (1979), supra, and having the following sequences: 5'-TTCCCAACCATT-3'. This 12-mer sequence matches a coding sequence in the hGH sequence. It corresponds to the codons for the first four amino acids of the mature hGH protein sequence (see Martial, J. A., Hallewell, R. A., Baxter, J. D., and Goodman, H. M., *Science* 205:602–607, (1979)), which are Phenylalanine-Proline-Threonine-Isoleucine (Phe-Pro-Thr-Ile). The 12-mer primer was mixed with BamHI-digested p20C4 plasmid DNA to convert the DNA sequence coding for human growth hormone into a more convenient structure for further manipulations.

The methods used for this conversion are described by Goeddel, D. V., Shepard, H. M., Yelverton, E., Leung, D., and Crea, R., *Nucleic Acids Research* 8:4057–4074 (1980). Essentially the primer was used to adapt the human growth hormone gene with a new sequence as Goeddel, D. V., Shepard, H. M., Yelverton, E., Leung, D., and Crea, R., *Nucleic Acids Research* 8:4057–4074 (1980), had done in adapting the interferon gene. The mixture containing primer and plasmid DNA was denatured by heat and then treated with *E. coli* DNA polymerase I Klenow fragment and the dNTP's, as described in Goeddel, et al. (1980), supra. The DNA was then digested with SmaI enzyme. SmaI cuts hGH gene at the 3'-end of the gene (see Martial, et al. (1979), supra. A fragment of roughly 572 base pairs was purified from gel. The fragment has the nucleotide sequence starting from the first codon for the phenylalanine (Phe) in the mature human growth hormone protein, and ending at the 3'-end shortly after the coding sequence of hGH gene (see Martial, et al. (1979), supra.

Figure 4:
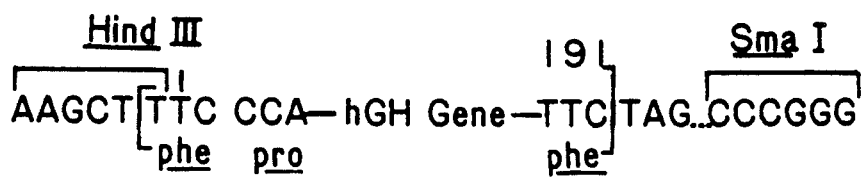
FIG. 4 shows the pertinent features of plasmid pSYC709.
Figure 4:
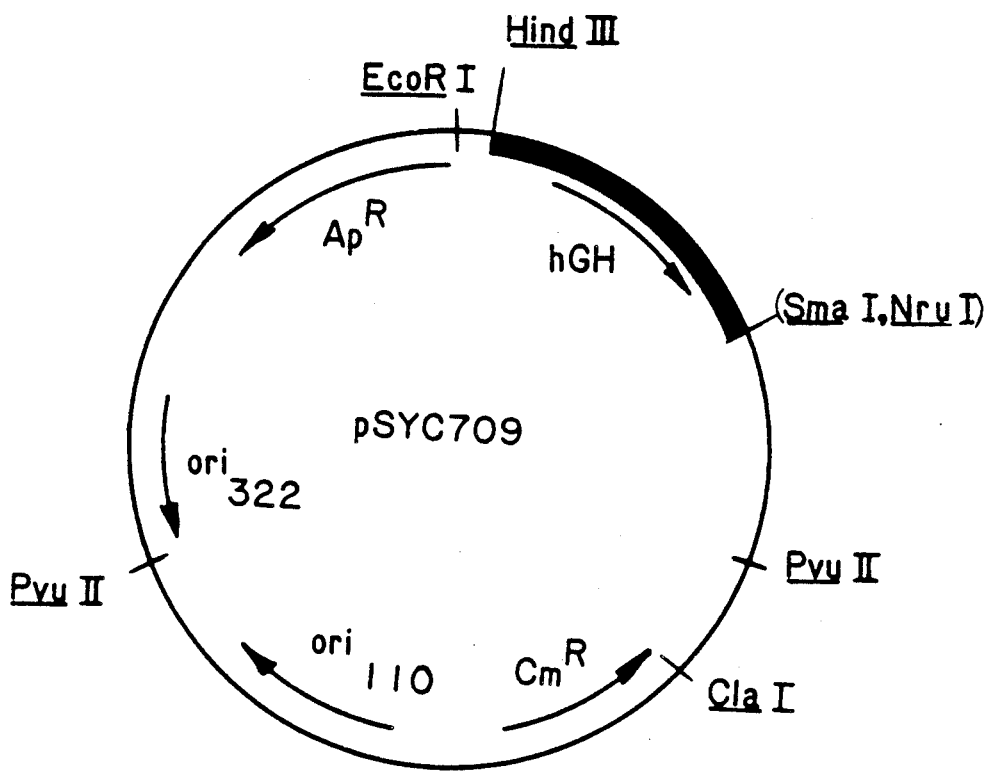

The vector DNA used to clone this fragment was pLP1201. Plasmid pLP1201 was derived from plasmid pDH5060 which in turn was derived as composite plasmid consisting of pBR322 and the Bacillus plasmid pOG1196, both of which were digested with PvuII and then ligated. Essentially plasmid pDH5060 is the same as pLP1201 except that one of the HindIII sites has been removed from pDH5060. The HindIII site removed is that in the portion of pDH5060 derived from pOG1196. pDH5060 was partially digested with HindIII. Staggered ends were filled in and religated. E. coli K-12/CS412 was transformed with the resuling plasmids. Transformants were selected by resistance to ampicillin and tetracycline. Selected cells were found which harbored a plasmid, pLP1201, with a single HindIII site, that derived from the pBR322 fragment in pDH5D60. Plasmid pLP1201 was digested with HindIII enzyme and NruI enzyme, both of which cut the sequence derived from pBR322. This linearized DNA was further treated with DNA polymerase I Klenow fragment in the presence of the four dNTP's to generate bluntended fragments. The large fragment from pLP1201 DNA so treated was purified on gel, and then ligated with the treated human growth hormone sequence, described above, using blunt-ended ligation conditions described by Maniatis, et al. (1982), supra. The resulting plasmids were used to transform E. coli K-12 strain CS412. Transformants which were phenotypically ampicillin-resistant and tetracycline-sensitive were further characterized by restriction analyses. One clone harbored a plasmid, designated pSYC709, which is shown in FIG. 4. pSYC709 has a unique HindIII site as a result of the cloning which joined the hGH gene to the vector DNA. This plasmid also has a unique EcoRI site. Both the EcoRI and HindIII sites can be cleaved and new fragments inserted which will be located upstream to the coding sequence of human growth hormone gene. This construction facilitates further expression work.

EXAMPLE VI

Construction of Plasmids Containing Fusion Genes between DNA Sequence Coding for Penicillinase Signal Peptide and Mature hGH Gene. Plasmids pSYC728 and pSYC744.

Construction of plasmid pSYC709, which contains the coding sequence for mature gGH gene, is described in Example V. This plasmid replicates in both B. subtilis and E. coli. Two unique sites exist upstream from the hGH gene, i.e,. an EcoRI site and a HindIII site. Plasmid pSYC709 was digested with HindIII enzyme. Then, half the sample was treated with E. coli DNA polymerase I Klenow fragment in the presence of the four dNTP's to fill-in the ends; the other half of the preparation was digested with S1 nuclease to remove single strand protruding ends. Both preparations were then further digested with restriction enzyme EcoRI. The large DNA fragments generated from these treatments were fractionated on a 0.8% agarose gel and purified after electrophoresis. The two preparations purified by these methods are: (A) the large fragment of pSYC709 which contains the EcoRI-generated end and a HindIII-generated end which has been filled in; and (B) the large fragment of pSYC709 which contains an EcoRI-generated end and a S1-treated HindIII-generated end.

In a separate experiment, DNA fragments which contain the penP promoter and the coding sequence for the signal peptide were prepared. Plasmid pDH5508, described in Example IV, was digested in one experiment with NaeI. In another experiment it was digested with HpaII and the HpaII digested preparation was treated with S1 nuclease to generate blunt-ended fragments by removing protruding ends. These DNA preparations were then further digested with restriction enzyme EcoRI. The fragment which contains penicillinase promoter and DNA sequence coding for signal peptide was purified from each of the two pDH5508 digests after fractionation on gels. The penP fragment generated by EcoRI and NaeI digestions was used to construct plasmid pSYC744. The fragment generated by EcoI enzyme and HpaII enzyme (followed by S1 nuclease treatment) was used for the construction of plasmid pSYC728.

To construct plasmid pSYC728, the A fragment (the large fragment of pSYC709 prepared as described supra), and the EcoRI to HpaII penP fragment from pDH5508 were used. The fragments were ligated together and resulting plasmids transformed into E. coli K-12/CS412 cells. The EcoRI to NaeI penP fragment from pDH5508 and the B fragment (which was prepared from pSYC709 as described supra) were used in a similar fashion. These fragments were ligated and transformed into E. coli K-12/CS412 cells. Transformants resistant to ampicillin were selected from these experiments and the DNA's analyzed after purification. One clone generated from the first experiment contained a plasmid designated pSYC728 and one clone from the second expreiment contained a plasmid designated as pSYC744. They have essentially the structure as shown for plasmid pSYC709 in FIG. 4 except the region 5' to the hGH gene was altered. The original EcoRI to HindIII site region of pSYC709 was replaced in both plasmids by a fragment which contains the sequence of penicillinase promoter and the signal peptide. For plasmid pSYC728 (as shown in FIG. 6), the sequence at the penP-hGH junction is GCAGCTTTC. The GCA corresponds to the codon for the last (34th) amino acid in the signal peptide. The GCT, derived from the repaired HindIII site, codes for alanine (Ala). The TTC codes for the N-terminal Phe of mature hGH. Since the sequence GCAGC is recognized by Fnu4H1 restriction enzyme, plasmid pSYC728 was digested with Fnu4H1 enzyme. The presence of a site for this enzyme at the expected location in the signal peptide coding sequence was identified. This proved that the fused-penP-hGH gene on pSYC7 has the expected junction sequence as indicated above and in FIG. 6.

For plasmid SYC744 a different method was used to prove that the sequence is correct. It has the expected sequence GAATGCCTTC at the penP-hGH gene junction, which corresponds to the coding sequence for the last nucleotide of 32nd, the entire 33rd, and the entire 34th codons for the signal sequence and the first codon in the sequence for the mature hGH protein. Since restriction enzyme XmnI recognizes the GAANNNNTTC sequence, plasmid pSYC744 was digested with XmnI enzyme. The presence of the restriction site was found in the expected location. This substantiated the sequence in pSYC744 as indicated above and shown in FIG. 6.

EXAMPLE VII

Construction of Plasmid pSYC720 which Carries a Sequence for a Modified penP Signal Peptide Fused to a Coding Sequence for hGH.

Plasmid pSYC660 (Example II) was digested with BamHI enzyme which cuts at a position corresponding to the codons for the 26th and the 27th amino acids of the signal peptide. The DNA ends were repaired with DNA polymerase I Klenow fragment and dNTP's and then digested again with EcoRI enzyme. The fragment containing penP promoter and a portion of the sequence for signal peptide was purified by gel elution and was ligated with a fragment of pSYC709 (Example V) which had been made by digesting pSYC709 with HindIII enzyme, then blunt-ending by filling in with Klenow fragment and dNTP's, then digesting with EcoRI. Ligation of the EcoRI to repaired-BamHI, penPS27-containing fragment derived from pSYC660 and the large EcoRI to repaired-HindIII fragment of pSYC709 was performed with T4 ligase and the mixture used to transform E. coli competent CS412 cells. One ampicillin-resistant transformant which harbors plasmid pSYC720 was further characterized. It carries the penP promoter and codons for the first 28 amino acids of the modified signal peptide derived from the penP $S_{27}$ gene, followed by codons for the Phe-Pro—sequence found in the mature growth hormone protein. The signal sequence - hGH junction region of the fused gene on pSYC720 is shown in FIG. 6.

EXAMPLE VIII

Use of in vivo Recombination to Create Fusion Genes Carrying DNA Sequence for Modified penP Signal Peptides Fused to the Sequence Coding for Mature Plasmids pSYC748 and pSYC778.

In order to introduce the cysteine$_{27}$-serine$_{27}$ mutation into fusion genes, a method which involves the transformation of heteroduplex DNA made between single-stranded DNA from a pair of parental plasmids to produce recombinants in vivo was utilized.

Construction of plasmids pSYC728 and pSYC744, which carry the fusion gene coding for the wild-type signal sequence of penP and the protein sequence of hGH, are described in Example VI. Similar constructs have been prepared using signal peptide coding sequence from modified penP which has the ser$_{27}$ mutation. These are plasmids pSYC778 and pSYC748; they are derived from plasmids pSYC728 and pSYC744, respectively. These plasmids are illustrated in FIG. 6. In constructing these plasmids, a method was used which allows in vivo genetic recombination in heteroduplexed plasmids. To achieve this, plasmids pSYC716 and pSYC742 were made.

Plasmid pSYC716 was constructed by cloning a fragment containing modified penP signal sequence (ser27 mutation), obtained from plasmid pSYC660, into plasmid pBR322. The pBR322 vector DNA was first digested with ClaI and EcoRI enzymes and this DNA was then repaired with DNA polymerase I Klenow fragment in the presence of the four dNTP's to generate blunt-ends on the DNA fragments. In a separate experiment, plasmid pSYC660, which is identical to plasmid pSYC310-2, see McLaughlin, et al. (1982), supra, except that the Cys$_{27}$ to Ser$_{27}$ mutation in penPS$_{27}$ has been introduced into this plasmid, was digested with AluI enzyme and AvaI enzyme. AluI recognizes multiple sites in the plasmid, including the HindIII site as described in McLaughlin, et al. (1982), supra. AvaI is located in the coding sequence corresponding to the codons for the 61st and 62nd amino acids in the penP gene (see Kroyer, J., and Chang, S., (1981),(supra.1. The digested DNA fragments were then repaired by DNA polymerase I Klenow fragment to generate blunt-ends on all the fragments. The fragment containing penP promoter and the coding sequence for the first 62 amino acids was isolated after fractionation on gel (using gel elution). This purified AluI-AvaI fragment (wherein the AluI-end is from the HindIII site on pSYC660 was ligated with pBR322 DNA which has been previously digested with EcoRI and ClaI enzymes and blunt-ended with DNA polymerase I Klenow fragment and the dNTP's as described supra. Resulting plasmids were transformed into E. coli K-12/CS412 cells, and an ampicillin-resistant and tetracycline-resistant transformant was isolated from which a plasmid, designated as pSYC716, was identified. It contains the pBR322 sequence, except that the region between the (repaired) EcoRI site and the (repaired) ClaI site has been replaced with the AluI-AvaI fragment from pSYC660 containing part of the penPS$_{27}$ sequence. The penPS$_{27}$-containing sequence in pSYC716 is now flanked by an EcoRI site, 5' from the 5'-end of the penPS$_{27}$ gene, and a HindIII site.

To construct plasmid pSYC742, plasmid pSYC716 was digested with EcoRI and HindIII enzymes. The small fragment, which contains penP promoter and the coding sequence for the first 62 amino acids of Ser-27 penicillinase was purified. Plasmid pSYC709 was digested with EcoRI and the HindIII enzymes and the digested DNA was ligated with the purified EcoRI to HindIII fragments derived from pSYC716. Upon ligation and transformation into competent CS412 cells, the purified plasmid DNA from one ampicillin-resistant transformant (designated the plasmid pSYC742) has the structure as expected. The short sequence located between the EcoRI and HindIII sites in pSYC742 contains penPS$_{27}$ sequence and is derived from pSYC716, and the large EcoRI to HindIII fragment is derived from pSYC709.

Parental plasmid pSYC742 was digested with HindIII enzyme to completion and the termini were blunt-ended by treatment with S1 nuclease to remove protruding ends.

Figure 3:
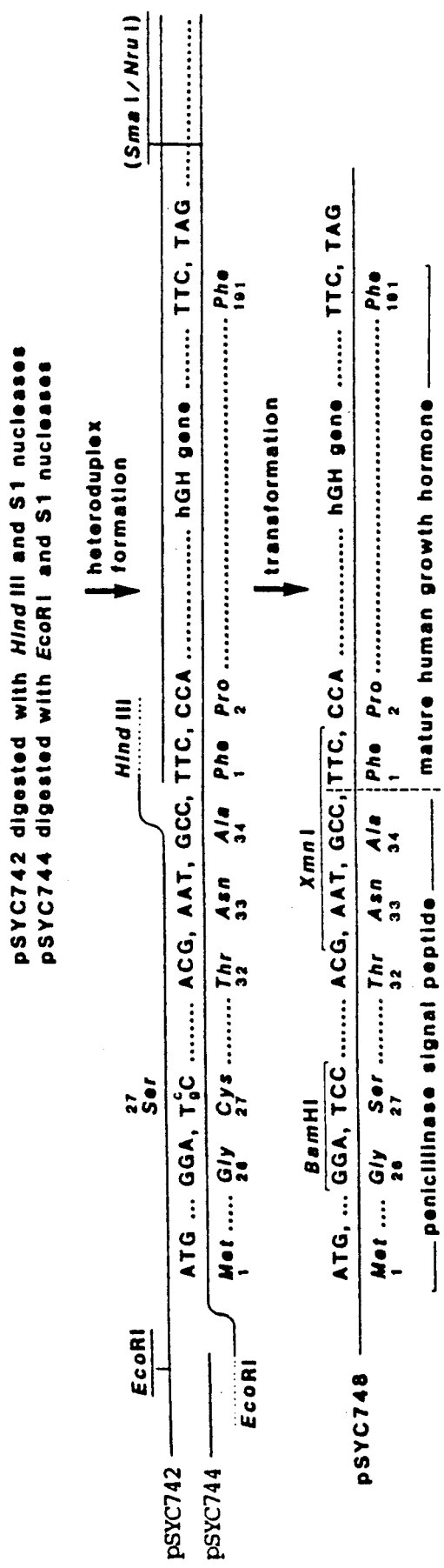
FIG. 3 is a codon diagram illustrating construction of pSYC748 by heteroduplex formation and in vivo recombination.

In a separate experiment, the second parental plasmid, plasmid pSYC744, was digested with EcoRI enzyme and blunt-ended by treatment with S1 nuclease. These two blunt-ended, linearized DNA's were mixed at approximately equimolar ratio (at a DNA concentration of about 10 micrograms per ml) and heated, by putting the test tube containing the DNA solution into a boiling water bath for 2 minutes, and slowly cooled (over several hours, to room temperature) to allow homoduplexes and heteroduplexes to form by annealing of the single strands formed by the heating. Homoduplexes have double-stranded duplex DNA wherein both strands are derived from the same parental plasmid, i.e., AA or A'A'. Because of the blunt-ending, the homoduplexes cannot recircularize. Heteroduplexes have double-stranded duplex DNA where each strand is derived from a separate parental plasmid, i.e., AA' or A'A. The heteroduplexes between pSYC742 and pSYC744 circularize. One form of the heteroduplexes which form is shown in FIG. 3. As indicated in the figure, there are hanging tails, single-stranded gaps, and a mismatch at the middle nucleotide in the codon for amino acid 27.

The mixture of homoduplexed and heteroduplexed, circularized DNA's was used to transform *E. coli* K-12/CS412 cells., the linear, homoduplexes transform with a frequency less than about 0.01 that of the heteroduplex circles. Ampicillin-resistant transformants were selected on plates and one of the transformants was characterized further. A plasmid from this transformant, designated plasmid pSYC748, has a structure, illustrated in FIG. 3, similar to that of plasmid pSYC744, resulting from in vivo removal of hanging tails, filling in of single-stranded gaps, and mismatched correction. By correction of the mismatch at position 27, pSYC748 has acquired a BamHI site indicating the presence of the $Ser_{27}$ mutation in this gene. The incorporation of the $Ser_{27}$ mutation is a result of transformation by heteroduplex DNA which has a mismatched base pair at the coding sequence corresponding to wild-type base pair at this location. Plasmid pSYC742 has a TCC codon for serine at this position, while plasmid pSYC744 has a TGC codon which codes for cysteine. DNA repair processes in vivo corrects the mismatch according to the DNA sequence on either one of the two strands present in the heteroduplex. The plasmid containing the $Ser_{27}$ mutation (pSYC748) was identified by the presence of a new BamHI site.

Using a similar procedure, heteroduplex recombination was performed between plasmid pSYC742 and plasmid pSYC728. pSYC728 was linearized with EcoRI and blunt-ended with S1 nuclease treatment. pSYC742 was linearized with HindIII and blunt-ended with $S_1$ nuclease treatment. Heteroduplex recombination was then carried out with the resulting linear fragments, as described above for pSYC742 and pSYC744. *E. coli* K-12/CS412 and ampicillin-resistance were used for transformation and selection. Again, in vivo, hanging tails were removed, single-stranded gaps were filled in, and the mismatch (at position 27) was corrected. A plasmid, designated pSYC778, was isolated from an ampicillin-resistant transformant. pSYC778 has a sequence similar to that of pSYC728, except that pSYC778 has acquired the $Ser_{27}$ mutation. Therefore using this in vivo recombination procedure, two derivative recombinant plasmids were constructed, each of which carries a fusion gene comprised of the signal peptide of $penPS_{27}$ and the coding sequence of mature hGH. In plasmid pSYC778 the fusion gene has a DNA sequence for the 34 amino acids of the $penPS_{27}$ signal peptide followed by sequence for alanine, and then phenylalanine and the rest of the hGH sequence. In plasmid pSYC748 the fusion gene has a DNA sequence for the 34 amino acids of the $penPS_{27}$ signal peptide followed by sequence for the complete, mature hGH protein. A portion of the fusion genes on pSYC748 and pSYC778 is shown in FIG. 6.

EXAMPLE IX

Additional Oligonucleotides for Primer-directed Mutagenesis.

The following oligonucleotides were prepared following the procedures of M. Matteucci and M. Carruthers, *J. Am. Chemical Soc.*, 103, 3185–3991 1981}with an automatic synthesizing machine (Model Sam One from Biosearch, Inc., San Rafael, California):

3'-GTCCTAGAGGATTGTT-5', designated oligonucleotide $S_{27}P_{28}$; and

3'-GCAGCGCGGTCTAGAACGTCCT-5', designated oligonucleotide PD24.

Further, the following oligonucleotide is prepared in the same manner as oligonucleotides $S_{27}P_{28}$ and $PD_{24}$:

3'-AACGTCCCCGCGGATTGT-5', designated oligonucleotide $A_{27}P_{28}$.

EXAMPLE X

Additional *B. licheniformis* 749/C Penicillinase Genes with Mutations in the DNA Sequence Coding for Signal Peptide and Vectors Comprising the Mutated Genes.

A. Mutant with Serine at Position 27 and Proline at Position 28 (pSYC947)

Primer directed mutagenisis was carried out, following the procedures of Example II, above (essentially those of Zoller and Smith 1981), supra, using *E. coli* JMI03, phage $M13penPS_{27}$ and RF-DNA and single-stranded DNA therefrom, and oligonucleotide $S_{27}P_{28}$, prepared as in Example IX, that had been 5'-phosphorylated, as primer. M13 RF-DNA was isolated in which the sequence 5'-TCCGCT-3' at codons 27 and 28 (i.e., codons corresponding to amino acids 27 (Ser}and 28 (Ala}in the signal sequence of the $Ser_{27}$-penicillinase) in the penicillinase gene had been changed, to 5'-TCTCCT-3', for Ser and Pro. Screening for such a mutant was carried out using the DNA-oligonucleotide hybridization probing technique as described in Zoller and Smith (1981), supra, at pp. 6492, 6493 and 6496, with radiolabeled oligonucleotide $S_{27}P_{28}$ as probe. Single-stranded DNA was isolated from phage in the supernatant of cultures of *E. coli* JMI03 that had been transformed with mutant, covalently closed, circular, double-stranded RF-DNA. Confirmation that the phage isolated by the screening procedure was the desired phage with $penPS_{27}P_{28}$ was obtained by restriction analysis of RF-DNA of the isolate phage. Such analysis revealed loss of a BamHI site, as expected. Codons for amino acids 26, 27 in $penPS_{27}$ are 5'-GGATCC-3'. This sequence is the recognition sequence for BamHI. Because, in $penPS_{27}P_{28}$, the codon for serine 27 is changed to TCT, the BamHI site is lost. The resulting phage is desginated $M13penPS_{27}P_{28}$.

Plasmid pSYC660, and as described above in Example II, was partially digested with BamHI, using the restriction enzyme under standard conditons for complete digestion but allowing the reaction to preceed for less than about half of the time required for complete digestion, and the sticky ends of the partially digested plasmids were repaired using *E. coli* DNA polymerase I Klenow fragment and required dNTP's. The resulting blunt-ended linearized plasmids were ligated using T4 DNA ligase. *E. coli* K-12/CS412 cells were transformed with resulting plasmids. Transformants were selected for ampicillin resistance and then screened for a plasmid with one BamHI site.

There are two BamHI sites in pSYC660: one at the codon for $serine_{27}$ in the $penPS_{27}$ gene (see Example II), supra) and the other at one end of the approximately 1.32 kbp (kilo base pair}HindIII-BamHI fragment which contains the $penPS_{27}$ gene. Plasmids cleaved, by the partial BamHI digestion, at the BamHI site at the $serine_{27}$ codon of $penPS_{27}$ would not have been ampicillin-resistant, as such resistance is provided by the penicillinase gene, which could not have been expressed after the gene had been cleaved and then religated (with repaired, blunted ends) as described above. Consequently, selection for ampicillin-resistance left only transformants with plasmids with the BamHI site at the serine$_{27}$ position in penPS$_{27}$ intact. Some of the selected transformants harbored plasmids that had lost the other BamHI site in pSYC660, i.e., the BamHI site at one end of the approximately 1320 bp HindIII-BamHI fragment. Screening of transformants for a plasmid with a single BamHI site resulted in isolation of plasmid pSYC667.

Plasmid pSYC667 is the same as pSYC660 except that, in place of the BamHI recognition sequence (5'-GGATCC-3') at the end of the approximately 1320 bp HindIII-BamHI fragment in pSYC660, pSYC667 has the sequence 5'-GGATCGATCC-3'.

Plasmid pSYC667 retains the PstI and BglII recognition sites of plasmid pSYC660 (see Example II supra). Similarly, the HindIII-BamHI fragment of M13penPS$_{27}$P$_{28}$ that contains the pen fragment of M13penPS$_{27}$P$_{28}$ that contains the penPS$_{27}$P$_{28}$ gene has a PstI site and BglII site at the same locations as the PstI site and BglII site, respectively, in the HindIII-BamHI-penPS$_{27}$-containing fragment in pSYC667.

pSYC667 was cleaved with PstI and BglII and the large fragment was isolated by gel elution.

M12penPS$_{27}$P$_{28}$ was cleaved with PstI and BglII and the small, penPS$_{27}$P$_{28}$ fragment-containing fragment isolated by gel elution.

The large PstI-BglII fragment from pSYC667 and small PstI-BglII fragment from M13penPS$_{27}$P$_{28}$ were ligated using T4 DNA ligase and resulting plasmids were transformed into E. coli K-12/CS412. Transformants were selected fOR ampicillin resistance. One selected transformant chosen for further study contained plasmid pSYC947 which, as expected, contains the penPS$_{27}$P$_{28}$ gene and no BamHI cleavage site. pSYC947 is identical to pSYC667 except that the penPS$_{27}$ gene in pSYC667 is replaced with pen PS$_{27}$P$_{28}$ in pSYC947.

A portion of the penPS$_{27}$P$_{28}$ gene on pSYC947 is illustrated in FIG. 5. The TCG codon with the circled "1" above it in the illustration of pSYC947 codes for the N-terminal serine of B. licheniformis large exopenicillinase. The horizontal lines in the illustration of pSYC947, to the left of TCTCCT, between CCT and TCG, and to the right of TCG, indicate nucleotide sequences identical to those in the same locations, in the wild-type gene, illustrated by the sequence indicated in FIG. 5 for pSYC310-2.

B. Mutant with Alanine at Position 27 and Proline at Position 28 (pSYC947A)

Using the procedures of Example X(A), supra, primer directed mutagenesis is carried out to prepare M13 phage, designated M13penPA$_{27}$P$_{28}$, carrying the penicillinase gene from B. licheniformis 749/C mutated at codon 26 from GGA for glycine to GGG for glycine, mutated at codon 27 from TCG for cysteine to GCG for alanine, and mutated at codon 28 from GCT for alanine to CCT for proline. The procedure is carried out using 5'-phosphorylated oligonucleotide A$_{27}$ P$_{28}$ from Example IX and DNA from phage M13penPA$_{27}$ (Example III). RFDNA of resulting phage M13penPA$_{27}$P$_{28}$ has an AluI restriction fragment of approximately 650 bp in length in place of two AluI restriction fragments of approximately 310 bp and 340 bp in length, in RF-DNA of phage M13penPA$_{27}$. Further, phage M13penPA$_{27}$P$_{28}$ RF-DNA contains a NarI restriction site which phage M13penPA$_{27}$ RF-DNA does not. These differences in restriction sites are apparent from a comparision of the sequences of codons for amino acids 26, 27 and 28 in penP A$_{27}$ (5'-GGAGCTGCT-3') and penP A$_{27}$ P$_{28}$ (5'-GGGGCGCCT-3'). These differences in restriction sites are used to identify phage that have acquired the A$_{27}$ P$_{28}$ mutation.

Plasmid pSYC310-2 is digested with HindIII and BamHI and the large fragment is isolated by gel elution.

M13penPA$_{27}$P$_{28}$ RF-DNA is digested with HindIII and BamHI and the approximately 1320 bp fragment containing penPA$_{27}$P$_{28}$ is isolated by gel elution.

The large HindIII-Bam,HI fragment from pSYC310-2 and approximately 1320 bp HindIII-BamHI fragment from M13penPA$_{27}$P$_{28}$ are ligated using T4 DNA ligase, and the resulting plasmids are transformed into E. coli K-12/CS412. Transformants are selected for ampicillin resistance. One ampicillin-resistant transformant is chosen for further study and found to contain a plasmid, pSYC947A, which has a NarI restriction fragment of about 1050 pb in length that is not found upon NarI digestion of plasmid pSYC660A, as expected because of the presence of the NarI site in the penPA$_{27}$P$_{28}$ gene on pSYC947A.

Part of the penPA$_{27}$P$_{28}$ gene on pSYC947A is illustrated in FIG. 5.

A polypeptide fused behind the alanine at position 34 in the signal sequence provided by penPA$_{27}$P$_{28}$ on pSYC947A, transformed into both E. coli and B. subtilis, would be secreted with higher efficiency . than the same polypeptide fused behind the alanine at position 34 in the signal sequence of wild-type penicillinase of B. licheniformis 749/C. The fraction of the penicillinase expressed by penPA$_{27}$P$_{28}$ on pSYC947A that is secreted, by both E. coli and B. subtilis, transformed with the plasmid would be higher than the fraction of the penicillinase, expressed by the wild-type penP gene, that is secreted in the respective species when transformed with a plasmid (e.g., pSYC310-2 containing the wild-type gene.

C. Mutant with the Dipeptide NH$_2$-ProAsp-CO$_2$H Inserted between Alanine at Position 23 and Leucine at Position 24 and with Serine Rather Than Cysteine at Position 27 (pSYC957)

Using the procedure of Example X(A), supra, primer directed mutagenisis was carried out to prepare M13 phage, designated M13penPS$_{27}$:: PD$_{24}$, carrying the penicillinase gene from B. licheniformis 749/C mutated by the insertion, between codon 23 (GCG) for alanine and codon 24 (CTT) for leucine, of two codons (5'-CCAGAT3') for proline and aspartic acid and further mutat (codon 29 in the mutated gene}from TCG (cysteine) to TCC (serine).

The procedure was carried out using 5'-phosphorylated oligonucleotide PD$_{27}$ from Example IX and DNA from phage M13penPS$_{27}$ (Example II).

RF-DNA of the M13 phage containing the desired penPS$_{27}$::PD$_{27}$ mutant gene would retain the BamHI site at codons 26 and 27 in penPS$_{27}$ (codons 28 and 29 in penPS$_{27}$::PD$_{24}$) and would have a BglII site at codons 24, 25 and 26 (5'-CCAGATCTT-3') Screening for phage with the desired mutant gene was carried out using the hybridization probe technique of Zoller and Smith (1981), supra, as in Example X(A), supra, with radiolabeled oligonucleotide PD$_{24}$. Confirmation that the phage isolated by the screening procedure was the desired M13penPS$_{27}$::PD$_{24}$ phage was obtained by restriction analysis of RF-DNA of the phage, which revealed the additional, expected BglII site, as compared with M13penPS$_{27}$ or M13-CM1 RF-DNA.

Plasmid pSYC667 from Example X(A), supra, was digested with BamHI and partial digested with HindIII and the large fragment isolated by gel elution. (Partial digestion was by reaction under standard conditions for complete digestion, but for a time limited to less than half of that requried for complete digestion.)

RF-DNA of phage M13penPS$_{27}$::PD$_{24}$ was digested with BamHI and HindIII and the small, approximately 320 bp fragment, containing the penP promoter and coding sequence for the first 28 amino acids in penPS$_{27}$::PD$_{24}$ signal peptide, was isolated by gel elution.

The large HindIII-BamHI fragment from pSYC667 and small BamHI-HindIII fragment, described in the previous paragraph, from M13penPS$_{27}$::PD$_{24}$ RF-DNA were ligated using T4 ligase. E. coli K-12/CS412 were transformed with the resulting plasmids, and transformants were selected from ampicillin resistance and chlorampenicol resistance. One ampicillin-resistant, chlorampenicol-resistant transformant was chosen for further study and found to contain a plasmid, pSYC957, which is identical to plasmid pSYC667 except that the penPS$_{27}$ gene in pSYC667 is replaced with the penPS$_{27}$::PD$_{24}$ gene in pSYC957.

A part of the penPS$_{27}$::PD$_{24}$ gene on plasmid pSYC957 is illustrated in FIG. 5.

EXAMPLE XI

Additional Fused Genes, Comprising Sequences Coding for Modified B. licheniformis 749/C Signal Peptides and a Sequence Coding for Human Growth Hormone, and Plasmids Comprising the Fused Genes.

A. Plasmid with Sequence, Coding for the 30 N-terminal Amino Acids of the Signal Sequence Coded by penPS$_{27}$::PD$_{24}$, Fused to a Sequence Coding for Human Growth Hormone (pSYC970)

Plasmid pSYC957 comprising penPS$_{27}$::PD$_{24}$ Example X(C)), was cleaved with BamHI, which has a unique site on the plasmid at codons 28 and 29 in penPS$_{27}$::PD$_{24}$. The resulting staggered ends were repaired with E. coli DNA polymerase I Klenow fragment and the four dNTP's. The resulting blunt-ended linearized plasmids were then cleaved with EcoRI, which also has a unique site on the plasmid, corresponding to the unique EcoRI site on plasmid pSYC310-2 (McLaughlin et al. (1982}, supra, which is related to pSYC957 through pSYC667 and pSYC660 (see Example II and Example X(C)). The small EcoRI to blunt-ended BamHI fragment was then isolated by gel elution.

Plasmid pSYC709 (Example V) was cleaved with HindIII, which has a unique site on the plasmid (see FIG. 4). The resulting staggered ends were repaired with E. coli DNA polymerase I Klenow fragment and the four dNTP's. The blunt-ended linearized plasmid was then cleaved with EcoRI at its unique site (see FIG. 4).

The small EcoRI to blunt-ended BamHI fragment from pSYC957 was mixed with the EcoRI-blunt-ended HindIII fragments from pSYC709 and ligation was carried out using T4 DNA ligase under conditions suitable for blunt-end ligation. The resulting mixture was used to transform E. coli K-12/CS412 and transformants were selected for ampicillin-resistance. One ampicillin-resistant transformant was chosen for further analysis and found to harbor pSYC970.

Plasmid pSYC970 is illustrated in FIG. 6. It is the same as pSYC720 except that the mutant penicillinase signal sequence coded by pSYC970 has two more amino acids, proline at position 24 and aspartic acid at position 25, than the mutant penicillinase signal sequence coded by pSYC720.

The sequence on pSYC970, which codes for signal peptide and is fused to the sequence for human growth hormone, codes for the first 30 N-terminal amino acids of the signal peptide coded by penPS$_{27}$::PD$_{24}$.

The human growth hormone secreted by E. coli and B. subtilis transformed with pSYC970 is mature human growth hormone, with Nterminal Phe.

B. Plasmid pSYC962 with Sequence, Coding for the Signal Peptide Coded by penPS$_{27}$P$_{28}$ with an Additional Alanine at the Carboxy-Terminus of Said Signal Peptide, Fused to a Sequence Coding for Human Growth Hormone.

Plasmid pSYC947 (Example X) was digested with restriction enzymes EcoRI and MspI. The plasmid has a unique EcoRI site corresponding to the unique EcoRI site in pSYC310-2. The plasmid also has an MsoI site (also HpaII site) at the codons corresponding to amino acids 71 and 72 in prepenicillinase (see J. Kroyer and S. Chang (1981), supra). The approximately 450 bp EcoRI-MspI fragment was isolated by gel elution.

Plasmid pSYC709 (Example V) was digested at its unique EcoRI site (see FIG. 4) and then digested at its unique ClaI site, which is between the EcoRI and HindIII sites in FIG. 4. The 450 bp EcoRIMspI fragment from pSYC947 was added to the EcoRI-ClaI-digested pSYC709 and ligation was carried out using T4 DNA ligase. E. coli K-12/CS412 was transformed with the resulting plasmids and transformants were selected for ampicillin-resistance. One ampicillin-resistant transformant was examined further and found to contain a plasmid, designated pSYC956, with the expected insert between the EcoRI and ClaI sites of pSYC709.

pSYC956 has the same sequence between its unique EcoRI site and its pSYC709-derived HindIII site as pSYC778 has between its unique EcoRI site and the codon GCT corresponding to the alanine at position 35 in the illustration of pSYC778 in FIG. 6, except that: (i) pSYC956 has a sequence coding for the signal peptide coded by penPS$_{27}$P$_{28}$ (see pSYC947 in FIG. 5}, while pSYC778 has a sequence coding for the signal peptide coded by penPS$_{27}$ (see pSYC660 in FIG. 2), this difference involving a change from TCT CCT at codons 27 and 28 in the signal sequence code in pSYC956 to TCC GCT in the codons at the same positions in pSYC778; (ii) pSYC956 has 117 bp between the codon for alanine at position 34 in the modified signal sequence and the codon, GCT, for alanine that immediately precedes the codon TTC for the N-terminal phenylalanine of mature human growth hormone in both pSYC956 and pSYC778, while pSYC778 lacks these 117 bp (which code for the first 38 N-terminal amino acids of large exopenicillinase from B. licheniformis 749/C (see Kroyer and Chang (1981), supra}1 and, at the 3'-end, a translation termination signal (UAA); and (iii) pSYC956 has approximately 30 bp between its EcoRI site and the C of its pSYC947-derived HindIII site that are not present immediately after the T of the EcoRI site of pSYC778 that is closest to the penP promoter on the plasmid.

Plasmid pSYC956 was linearized with EcoRI and resulting protruding ends were removed by treatment of the DNA, at 50 microgram/ml, for 30 minutes at 22° C., with S1 nuclease (220 U/ml) in pH 4.6 buffer containing 300 mM NaCl, 60 mM ZnSO4 and 50 mM Na-.acetate. See Maniatis et al. (1982), p. 140. After the 30 minute period, DNA was phenol-extracted and ehtanol-precipitated.

Plasmid pSYC778 was linearized with BamII (at a site in the hGH coding sequence) and resulting protruding ends were removed with S1 nuclease, in the same way as the protruding ends of ECoRI-cleaved pSYC956. After the S1 nuclease treatment, DNA was phenol-extracted and ethanol-precipitated.

The DNA pellets from pSYC956 and pSYC778 were resuspended together, to 25 microgram/ml of each, in annealing buffer, pH 7.5, containing 20 mM Tris, 100 mM NaCl, and 0.5 mM EDTA. The solution, in a 1.5 ml Eppendorf tube, was heated for one minute in a boiling water bath, then held for an additional 1-3 mintues in 90° C. bath, and then cooled slowly, over a period of 4 hours, to 30° C. This treatment resulted in the formation of heteroduplex circular DNA's (as well as homoduplexes; which, on account of the blunt-ending of the linearized plasmids, could not recircularize).

The mixtures of DNA's containing heterodouplex circles was used to transform *E. coli* K-12/CS412, wherein recombinant plasmids were formed during in vivo repair of the heteroduplexes. Transformants were selected for ampicillin resistance. Several ampicillin-resistant transformants were selected for further study. One harbored a plasmid, pSYC962, which is identical to plasmid pSYC778 except that the codons TCC GCT (Ser-Ala) for the 27th and 28th amino acids in the modified penP gene on pSYC778 are replaced with codons TCT CCT (Ser-Pro) in the modified penP gene on pSYC962. See FIG. 6.

Plasmid pSYC962 can also be formed, using the foregoing heteroduplexing procedure, with pSYC956 cleaved with EcoRI and then blunt-ended with *E. coli* DNA polymerase I Klenow fragment with the four dNTP's, rather than with S1 nuclease, and pSYC778 cleaved with BglII and also blunt-ended using Klenow fragment with ATP and TTP in place of S1 nuclease digestion.

C. Partition-proficient Plasmid with Sequence, Coding for the 28 N-terminal Amino Acids of the Signal Sequence Coded by penPS27, Fused to a Sequence Coding for Human Growth Hormone (pSYC852).

To be stably maintained in a culture of growing cells, a plasmid must either be "partition proficient", such that each daughter of every dividing cell receives at least one copy of the plasmid, or must provide a phenotype which the cells in the culture must have to survive under the culture conditons.

Typically, a plasmid constructed using genetic engineering techniques comprises a gene or genes for resistance to antibootic(s), which are lethal to the cells, into which the plasmid is intended to be transformed, which do not harbor the plasmid with its antibiotic resistance gene(s). The plasmid is maintained in cultures of growing cells by having an antibiotic (for which a gene on the plasmid provides resistance) in the culture medium. Only cells with the plasmid survive. If the antibiotic is eliminated from the culture medium, the percentage of cells in the culture which harbor the plasmid will decrease rapidly, typically to 0 within less than about 25 doublings but with widely varying rates, unless the plasmid is also "partition proficient".

Because antibiotics are expensive and complicate purification procedures for products (e.g., proteins for food or therapeutic uses) made by cells transformed with genetically engineered plasmids, it is advantageous to use such plasmids which are "partition proficient" and which, consequently, will be maintained stably in a culture of growing cells without the need for antibiotic in the culture medium.

Partition proficiency in *E. coli* is imparted to plasmids by a short DNA fragment identified by Meacock and Cohen, *Cell*, 20, 529-542 (1980).

Partition proficiency in Gram positive bacteria, including *B. subtilis*, is imparted to plasmids by a short DNA fragment (called herein the "par" fragment) located within an approximately 350 bp HindIII-HaeIII fragment on plasmid pOG2381, as disclosed in published European Patent Application 0 095 947, which is based on U.S. Pat. Application Ser. No. 470,576, filed Feb. 28, 1983, which in turn is assigned to the assignee of the instant application and is incorporated herein by reference.

The following procedure generated a par fragment containing sequence conveniently bounded by HindIII sites:

Plasmid pOG2326 was digested with BamHI and the staggered ends on the linearized plasmid were blunt-ended with *E. coli* polymerase I Klenow fragment and the 4 dNTP's. The blunt-ended linear fragment was then cleaved with HindIII at its unique HindIII site. The resulting mixture of linear fragments was combined with the approximately 350 pb HaeIII-HindIII, par fragment-containing sequence which had been isolated by gel elution from fragments of pOG2381 that had been digested with HindIII and HaeIII. The mixture of the 350 bp HaeIII-HindIII, par fragment-containing sequence and the two HindIII to blunt-ended BamHI fragments from pOG2326 was ligated with T4 DNA ligase under conditons suitable for blunt-ended ligation. The resulting plasmids were transformed into *E. coli* K-12/CS412 and transformants were screened for a plasmid with a HindIII-BamHI fragment of nearly the same size as the HaeIII-HindIII par-containing fragment. (Joining a HaeIII-cut end to a blunt-ended BamHI-cut end regenerates a BamHI site.) Such a transformant was found and the desired plasmid isolated from it was designated pSYC676.

pSYC676 has a ClaI site a few bp from the HindIII site but outside the HindIII-BamHI fragment which contains par.

pSYC676 was linearized with BamHI, the protruding ends were filled in with *E. coli* polymerase I Klenow fragment and the 4 dNTP's and the terminis were then ligated using T4 DNA ligase under conditions for blunt-end ligation. The result of this procedure was conversion of the BamHI site (GGATCC) to a ClaI site (underlined) (GGATCGATCC). The resulting plasmid, designated pSYC676CLA, is digested with ClaI and the approximately 360 bp, par fragment-containing sequence isolated by gel elution and combined with pBR322 that has been cleaved with ClaI at its unique ClaI site. The fragments are ligated with T4 DNA ligase and resulting plasmids cloned into *E. coli* K-12/CS412. A plasmid, designated pSYC756BR, is isolated from an ampicillin-resistant transformant and, by restriction-site analysis, is found to have the following arrangement of ClaI and HindIII site bordering the par-containing fragment: ClaI - HindIII—par—ClaI-HindIII.

In the construction of a plasmid such as pSYC756BR, with a CalI-HindIII—par—ClaI-HindIII fragment, any plasmid with a unique ClaI site and a HindIII site, preferably unique and within about 10 bp of the ClaI site, could be used in place of pBR322. One such alternative is pJH101, described in Jour. Bacteriol. 154, 1513–1515 (1983).

pJH101, cleaved at its unique ClaI site, was used with ClaI-digested pSYC676CLA in the manner described above for pBR322 in the construction of pSYC756BR, to make a plasmid designated pSYC756. pSYC756 has an approximately 360 p ClaI-HindIII—par—ClaI-HindIII fragment identical to that on pSYC756BR.

The par-containing, HindIII-site-bounded fragment from pSYC756, isolated by gel elution of fragments from HindIII-digested plasmid, was mixed with pSYC720 (Example VII) that had been linearized with HindIII at its unique HindIII site. The mixture was ligated with T4 DNA ligase and resulting plasmids transformed into E. coli K-12/CS412. Transformants were selected for ampicillin resistance and screened for a plasmid with the par-containing fragment inserted between two HindIII sites. Such a transformant was found, and the plasmid it contained was designated pSYC852.

pSYC852 is illustrated in FIG. 6. It is identical to pSYC720 in sequence, but for the par fragment inserted into pSYC720's HindIII site, which is upstream of the penP promoter. The location of the HindIII site in relation to the location of the penP promoter on pSYC720 is the same as the location of the HindIII site in relation to the location of the penP promoter on pSYC310-2. See McLaughlin et al. (1982), supra.

pSYC852 is partition proficient.

When B. subtilis BD224 transformed with pSYC852 is cultured in broth lacking antibiotic, it produces as much human growth hormone as B. subtilis SCR667 transformed with pSYC720 produces when cultured in broth containing chloramphenicol. (pSYC720 has a chloramphenicol resistance gene derived from pSYC310-2.) pSYC720 is rapidly lost from B. subtilis cultures which contain no antibiotic; consequently, the production of human growth hormone per cell in such cultures declines as growth continues.

EXAMPLE XII

Fused Gene Comprising a Sequence Coding for the Serine$_{27}$ Modified B. licheniformis Signal Peptide and a Sequence Coding for Serine$_{125}$ Interleukin-2 Polypeptide.

Interleukin-2 (IL-2), also referred to as T-cell growth factor, is a lymphokine produced by lectin-or antigen-activated T cells. Like interferons, IL-2 augments natural killer cell activity and is useful in the treatment of neoplastic diseases. IL-2 also has a number of other therapeutic and diagnostic applications. D. Mark et al., European Patent Application 893 306 221.9; and D. Mark et al., U.S. Patent Application Ser. No. 564,224, filed Dec. 20, 1983 and incorporated herein by reference.

The nucleotide sequence of a gene coding for human IL-2, and preparation of an expression vector for production in bacteria of human IL-2 polypeptide with IL-2 biological activity, has been described by Taniguchi et al., Nature, 302, 305–310 (1983) and Mark et al., European Patent Application 83 306 221.9, supra, and U.S. Patent Application Ser. No. 564,224, supra.

Using techniques analogous to those illustrated in the present specification, a sequence coding for human IL-2-polypeptide is operably joined to a sequence co-dong for a modified signal peptide of the present invention, such as that on pSYC720 or pSYC778, and the fused gene, on a plasmid that can replicate in E. coli (e.g. E. coli K-12/MM294 or E. coli K-12/CS412)or B subtilis (e.g. B. subtilis BD224), is transformed into such a host in which the plasmid can replicate, and human IL-2 polypeptide is expressed and secreted in mature form.

EXAMPLE XIII

Analysis of Modified Signal Sequences for Secretion from E. coli and B. subtilis A. Transformation of E. coli All transformantions of E. coli with plasmids involved in this example, as well as those described elsewhere in the present application, were carried out by the technique of Cohen, Chang and Hsu, Proc. Natl. Acad. Sci., (U.S.) 69, 2110 (1973). See also Maniatis et al. (1982), supra at pp. 249–255.

B. Transformation of B. subtilis

All transformations of B. subtilis with plasmids involved in ths example, as well as those described elsewhere in the present application were carried out as follows, using a technique related to that described by Anagnostopoulos and Spizizen, J. Bacteriol., 741–746 (1961).

10 X Spizizen I Minimal Solution was prepared by mixing, in a total solutin volume of 1 liter made up with distilled water, 20 gm $(NH_4)_2SO_4$, 140 gm $K_2HPO_4$, 60 gm $KH_2PO_4$ and 10 gm Na.citrate.

Spizizen I Medium was prepared by mixing 2.05 ml of 1M $MgSO_4$, 6 ml of 50% (w/w) glucose; 5 ml of 10% (w/w) yeast extract., 5 ml of 2% (w/w) casein hydrolysate; for each amino acid required by the strain to be transformed, 2.5 ml of a 1% (w/w) solution of the amino acid., 50 ml of 10×Spizizen I Minimal Solution; and enough distilled water to bring the total solution volume to 500 ml. For B. subtilis BD224 and B. subtilis BD170, the required amino acids are threonine and tryptophan. B. subtilis SCR667 is an auxotroph and requires no amino acids in the Spizizen I Solution.

Spizizen II Medium was prepared by adding 0.25 ml of 1M $CaCl_2$ and 1 ml of IM $MgCl_2$ to 500 ml of Spizizen I Medium.

30 ml of Spizizen I Medium was inoculated with a colony or spores of the B. subtilis strain to be transformed and was grown overnight 16–20 hours) at 37° C.

15 ml of the overnight culture were then inoculated into 135 ml of Spizizen I Medium in a 2800 ml flask and grown at 37° C. The optical density at 600 nm (O.D.) of the culture was measured after 1.5 to 2 hours, and then every 15 minutes until the culture was found to be in late log phase on the basis of an increase in O.D. of less than 5% between 15-minute O.D. readings.

50 ml of late log phase culture was then inoculated into 450 ml of Spizizen II Medium in a 2800 ml flask and grown at 37° C. for 1.5 hours. After the 1.5 hour growth, cells were spun down by centrifugation at 5000 rpm for 10 minutes at 4° C.

The pellet from centrigufation was then resuspended in 45 ml of supernatant, to which 6 ml of 80% (v/v) sterile glycerol was then added, just prior to freezing the culture in a dry ice-ethanol bath (70° C.). The cells in the frozen culture are competent cells, suitable for transformation by the desired plasmid, as folows:

0.5 ml–0.6 ml of the frozen, competent-cell-containing culture was thawed on ice.

10 microliter to 50 microliter of solution containing the plasmid to be transformed into the cells was combined with the thawed culture. The resulting mixture was shaken at 37° C. for 2 hours, during which transformation of plasmids and expression of genes on them occurred.

Finally, for selection, small aliquots such as about 5 microliter to about 200 microliter of the culture of transformed cells were transferred to plates containing the desired antibiotic or antibiotics for selection.

For B. subtilis cells transformed with plasmids for which data are presented in this example, selection was carried out with chloramphenicol, present at 5 micrograms/ml on the plates.

C. Assay for Secretion from B. subtilis

B. subtilis cells transformed with a plasmid of interest were grown in L.B. broth, See Maniatis et al. (1982), supra, p. 440) containing chloramphenicol at 5 micrograms/liter with vigorous shaking at 37° C. until the O.D. (optical density at 600 nm) of the culture reached 1.0. Aliquots of culture were then removed for analysis of total (i.e. secreted as well as non-secreted) protein expressed by the gene comprising a sequence coding for the signal sequence being tested. Cells in retaining culture were then pelleted by centrifugation (using an Eppendorf microfuge for 20 seconds at room temperature). Under the conditions employed, there was no evidence of cell lysis, as revealed by comparison of protein patterns on gels prepared with proteins from the supernatant and the pellet, as well as by the absence of detectable amounts of several proteins, known to be intracellular, in the medium.

Samples were analyzed for hGH or penicillinase by the procedures in Section E of this example. The amount of desired protein (hGH or penicillinase) in the supernatant is the amount of secreted protein.

Total desired protein was determined by assaying for the hGH or penicillinase (by procedures in Section E of this example) in aliquots of culture removed prior to pelleting. To ensure that this method of determining total protein was accurate, the aliquots were first sonicated, the membrane and other cell debris was spun down, and the resulting supernatant was assayed for the protein.

With penicillinase, assays for the total of the protein wer also done without such sonication. Except with te penP delta 2428 signal sequence, pencillinase determinations with and without somication gave essentially the same results, indicating that the pencilllinase was secreted into the extracellular medium or bound to the (outside) surface of cells in a way that made it detectable by the assay techniques. With penP delta 2428 signal sequence, a considerable fraction of penicillinase remained intracellular or bound to cell membrane in a way that made it inaccessible for the assay unless sonication of cells was carried out.

D. Assay for Secretion from E. coli

E. coli cells transformed with a plasmid of interest were grown in L.B. broth containing ampicillin at 50 microgram/ml concentration with vigorous shaking at 37° C. until the O.D. at 600 nm of the cultures reached 1.0.

Samples were assayed for the desired protein (penicilinase or hGH) using the methods in Section E of this example.

The amount of desired protein found in the periplasmic space of the cells (i.e., operationally, osmotic shocnate of the cells) is secreted protein. Osmotic shockate was prepared essentially by the procedure of Nosel and Heppel, J. Biol. Chem., 241, 3055-3062 (1966). Cells from an aliquot of the culture at O.D.=1.0 were pelleted by centrifugation and resuspended in a volume, one-tenth that of the aliquot, of buffer at pH 7.4 consisting of 50 mM Tris, 2.5 mM EDTA and 2% (w/v) sucrose. After 10 minutes at 23° C., cells were pelleted by centrifugation and then resuspended by vortexing in an equal volume of cold (approximately 2° C.) deionized water; the solution was then allowed to sit at 4° C. for 10 minutes. Finally, the cells were pelleted and the supernatant, which contains the osmotic shockate, was analyzed for the desired proteins.

Alternatively, Lunn and Pigiet's modified procedure was used to obtain osmotic shockate. Lunn and Pigiet, J. Biol. Chem., 257, 11424–11430 (1982).

To determine total of the desired protein (penicillinase or hGH) expressed in E. coli from the gene comprising a sequence coding for the signal peptide of interest, the cell material pelleted as the final step in preparation of osmotic shockate was assayed for the desired protein. This pelleted material was resuspended in a volume of buffer (pH 7.4, 50 mM Tris, 2% (w/v) sucrose and 2.5 mM EDTA, as above) equal to one tenth that of the volume of the aliquot of culture which was originally taken to prepare osmotic shockate. The resulting solution was first sonicated and then assayed for the desired protein.

Total of the desired protein is the amount found in the osmotic shockate plus the amount found in the resuspended cell material that had been pelleted as the final step in preparing the osmotic shockate.

E. Analysis Procedures for Human Growth Hormone and Penicillinase

The amount of human growth hormone expressed and secreted by E. coli and B. subtilis was assayed by radioimmunoassay (RIA) using hGH RIA kits available from Cambridge Medical Diagnostics Inc., Billerica, Massachusetts.

The amount of penicillinase expressed and secreted by E. coli and B. subtilis was determined either by the method of Schinder and Huber, in Enzyme Inhibitors, U. Brodbeck, editor, Verlas Chemie, Weinheim, W. Germany, pp. 169-176 (1980) PADAC (7-(thienyl-2-acetamido)-3(2(4-N,N-dimethylamino-phenylazo)-pyridinium methyl)-3-cephem-4-carboxylic acid) purchased from Calbiochem Inc., La Jolla, California, or by the mewthod of O'Callaghan et al., Antimicrob. Ag. Chemother., 1, 283-288 (1972), conducted at 21° C. rather than 37° C. and using nitrocefin (chromogenic cephalosporin 87/312) provided by Glaxo Research Ltd., Greenford, U.K.

F. Results—Human Growth Hormone

TABLE I

Human Growth Hormone Expressed in and Secreted from B. subtilis Transformed with Various Plasmids

| Plasmid | (nanograms hGH per O.D. unit (600 nm) cells) | | Fraction Secreted |
|---|---|---|---|
| | Total hGH | Secreted hGH | |
| pSYC709 [a] | <5 | <5 | — |
| pSYC720 [a] | 107 | 53 | 0.49 |
| pSYC970 [b] | 496 | 86 | 0.17 |
| pSTC744 [a] | 716 | 26 | 0.04 |
| pSYC748 [a] | 1266 | 66 | 0.05 |
| pSYC728 [a] | 380 | 20 | 0.05 |
| pSYC778 [a] | 608 | 118 | 0.19 |
| pSYC962 [b] | 282 | 49 | 0.17 |

TABLE I-continued

Human Growth Hormone Expressed in and Secreted from B. subtilis Transformed with Various Plasmids

| Plasmid | (nanograms hGH per O.D. unit (600 nm) cells) | | |
|---|---|---|---|
| | Total hGH | Secreted hGH | Fraction Secreted |
| pSYC852 [c] | 112 | 46 | 0.42 |

[a] Averages of at least 3 determinations. Strain transformed was B. subtilis SCR667.
[b] Averages of at least 2 determinations. Strain transformed was B. subtilis SCR667.
[c] Strain transformed was B. subtilis BD224, grown without antibiotic in the growth medium.

TABLE II

Human Growth Hormone Expressed in and Secreted From E. coli K-12/CS412 Transformed with Various Plasmids

| Plasmid | (nanograms hGH per O.D. unit (600 nm) cells) | | |
|---|---|---|---|
| | total hGH | Secreted hGH | Fraction Secreted |
| pSYC709 [a] | <5 | <5 | — |
| pSYC720 [a] | 1128 | 883 | 0.78 |
| pSYC970 [b] | 690 | 400 | 0.58 |
| pSYC744 [a] | 674 | 64 | 0.09 |
| pSYC748 [a] | 792 | 680 | 0.86 |
| pSYC728 [a] | 625 | 51 | 0.08 |
| pSYC778 [a] | 504 | 400 | 0.79 |
| pSYC962 [b] | 1380 | 120 | 0.09 |

[a] Averages of at least 3 determinations
[b] Single determination

E. Coli K-12/CS412 transformed with pSYC720 was grown with tritiated phenylalanine in the growth medium, and human growth hormone was isolated from osmotic shockate and is N-terminal amino acid sequence was determined. Radioactive phenylalanine was found at positions 1, and 10, as expected for naturally occurring, mature human growth hormone.

G. Results—B. licheniformis Penicillinase

TABLE III

B. licheniformis Penicillinase Expressed in and Secreted from B. subtilis BD224 Transformed with Various Plasmids

| Plasmids | (units penicillinase activity per O.D. unit c(600 nm) cells) | | |
|---|---|---|---|
| | Total Penicillinas [a] | Secreted Penicillinase | Fraction Secreted [b] |
| pSYC310-2 | 8.7 (8.0) | 6.8 | 0.78 |
| pSYC617 | 1.5 (0.7) | 0.6 [c] | 0.4 [c] |
| pSYC660 | 8.3 (7.9) | 7.5 | 0.90 |
| pSYC947 | | | approx. 0.9 [d] |
| pSYC957 | | | approx. 0.1 [d] |

[a] Amount in parentheses is without sonication.
[b] Amount secreted diveded by total amount.
[c] The membranes of the cells appeared to have been weakened by the penP delta 2428 gene on pSYC617, and the amount of penicillinase secreted probably represents, at least in part, protein from lysed cells.
[d] No quanitative data on total and secreted protein available. Numbers are based on qualitative comparisons of intensities of bands corresponding to penicillinase on gels of supernatant (for secreted protein) and culture (for total protein).

TABLE IV

B. licheniformis Penicillinase Expressed in and Secreted from E. coli Transformed with Various Plasmids

| Plasmid | Total Penicillinase | Secreted Penicillinase | Fraction Secreted |
|---|---|---|---|
| pSYC310-2 [a] | 1.7 | 0 | 0.00 |
| pSYC617 [a] | 5.5 | 0 | 0.00 |
| pSYC660 [a] | 5.4 | 4.3 | 0.80 |

[a] Transformed into either E. coli K-12/MM294 or E. coli K-12/CS412. Results do not differ significantly between these variants.

Availability of Plasmids and Microorganisms

The following are available from numerous sources, including the American Type Culture Collection, Rockville, Maryland (ATCC). They are deposited at ATCC under the numbers indicated:
B. licheniformis 749/C, ATCC No. 25972;
E. coli JMIOI, ATCC No. 33876;
E. coli JM103, ATCC No. 39463;
E. coli K-12/MM294, ATCC 33625;
pBR322, ATCC No. 37017; and
B. subtilis BD170, which could be used in place of B. subtilis BD224 and B. subtilis SCR667 with plasmids of the present invention which replicate in B. subtilis, ATCC No. 33608.

E. coli JM103 is also available from P-L Biochemicals, Inc. of Milwaukee, Wisconsin.

B. subtilis BD170 is also available from the Bacillus Genetic Stock Center, Department f Microbiology, Ohio State University, Columbus, Ohio (BGSC) under BGSC No. IA42.

The following have been deposited at the ATCC under the terms of the Budapest Treaty on the International Recognition of the Deposit of Microorganisms for the Purposes of Patent Procedure and Regulations promulgated thereunder:
pOG1196 in B. subtilis BD224, ATCC No. 31776;
pOG2165 in B. subtilis BD224, ATCC No. 31777;
pOG2381 in E. coli K-12/CS412, ATCC No. 39038;
pOG2326 in E. coli K-12/CS412, ATCC No. 39600;
pSYC310-2 in B. subtilis BD224, ATCC No. 39603;
pSYC709 in E. coli K-12/CS412, ATCC No. 39602;
pSYC756 in E. coli K-12/CS412, ATCC No. 39599;
pDH5452 in E. coli K-12/CS412, ATCC No. 39601;
E. coli K-12/MM294, ATCC No. 39607; and
B. subtilis SCR667, ATCC No. 39608.

E. coli K-12/CS412 cured of plasmid can be obtained by culturing any of the above-listed, plasmid-containing E. coli K12/CS412 in the absence of antibiotic. Similarly, B. subtilis BD224 cured of plasmid can be obtained by culturing any of the above-listed, plasmid-containing B. subtilis BD224 in the absence of antibiotic.

B. subtilis BD224 and B. subtilis SCR667 are also available from the BGSC under number IA46 and number IS53, respectively.

It may be seen therefore that the invention provides modified signal peptides derived from wild-type signal peptides of the type that are capable of forming membrane-bound lipoproteins. DNA sequences coding for the modified signal peptides are constructed by substituting the codon for at least the amino acid cysteine, found within the conserved region at the carboxy-terminal end or junction region of the signal peptide and modified in the formation of membrane-bound lipoprotein, with a codon for an amino acid other than cysteine that will not function to form membrane-bound lipoprotein. The modified signal peptides of the invention thus have an amino acid other than cysteine in place of the cysteine that is modified in membrane-bound lipoprotein formation. Modified signal peptides of the present invention are useful in obtaining secretion of desired proteins from cells in whch they are made. DNA sequences coding for the modified signal peptides are useful in cloning vectors. The invention further provides a method for producing recombinant plasmids in vivo.

Various modifications of the invention in addition to those shown and described herein will become apparent to those skilled in the art from the foregoing description and accompanying drawings. Such modifications are intended to fall within the scope of the appended claims.

What is claimed is:

1. A DNA sequence encoding a modified exo-signal peptide, said modified exo-signal peptide corresponding to a wild-type signal peptide which a) is capable of forming membrane bound lipoproteins and b) includes a facilitating region within the carboxy-terminal region thereof, wherein said wild-type signal peptide is a bacterial signal peptide selected from the group consisting of B licheniformis penicillinase signal sequence, E. coli lipoprotein signal sequence. Bacillus cereus penicillinase III signal sequence, and S. aureus penicillinase signal sequence said facilitating region comprising a tetrapeptide, selected from the group consisting of leu-ala-gly-cys and leu-ser-ala-cys, said facilitating region having a single cysteine, the presence of which is necessary for the formation of membrane bound lipoprotein, wherein the modification to said exo-signal peptide comprises another amino acid X in place in said cysteine of the facilitating region, said amino acid X not forming a membrane bound lipoprotein but forming substantially more exoprotein than said wild-type signal peptide sequence.

2. The DNA sequence of claim 1 wherein X is serine.

3. The DNA sequence of claim 1 fused to a DNA sequence encoding a desired protein.

4. The DNA sequence of claim 3 wherein the desired protein is a bacterial exopenicillinase, IL-2, or hGH.

5. A replicable expression vector effective in procaryotic host cells to express the DNA sequence of claim 3.

6. An expression vector replicable in procaryotic host cells comprising the DNA sequence of claim 3 operably linked to suitable control sequences.

7. Recombinant host cells transformed with the vector of claim 6.

8. A replicable expression vector capable in prokaryotic cells of effecting the production of a peptide and secretion of an exoprotein comprising a modified exosignal peptide operably linked to a desired protein, said modified exo-signal peptide corresponding to a wild-type signal peptide which is a) capable of forming membrane bound lipoproteins and b) includes a facilitating region within the carboxy terminal region thereof, wherein said wild-type signal peptide is a bacterial signal peptide selected from the group consisting of B licheniformis penicillinase signal sequence, E. coli lipoprotein signal sequence. Bacillus cereus penicillinase III signal sequence, and S. aureus penicillinase signal sequence, said facilitating region comprising a tetrapeptide selected from the group consisting of leu-ala-gly-cys and leu-ser-ala-cys, said facilitating region having a single cysteine, the presence of which is necessary for the formation of a membrane bound lipoprotein wherein the modification to said exo-signal peptide comprises another amino acid X in place of said cysteine of the facilitating region, said amino acid X not forming a membrane bound lipoprotein but forming substantially more exoprotein than said wildtype signal peptide sequence.

9. Recombinant host cells transformed with the vector of claim 8.

10. A method of effecting secretion of a desired protein sequence which method comprises culturing the transformed cells of claim 9 in suitable nutrient medium.

11. A method of obtaining secretion of a desired protein, which method comprises transforming prokaryotic host cells with a replicable expression vector capable in prokaryotic cells of effecting the production of a peptide and secretion of an exoprotein comprising a modified exo-signal peptide operably linked to a desired protein, said modified exo-signal peptide operably linked to a desired protein which is a) capable of forming membrane bound lipoproteins and b) includes a facilitating region within the carboxy terminal region thereof, wherein said wildtype signal peptide is a bacterial signal peptide selected from the group consisting of B licheniformis penicillinase signal sequence, E. coli lipoprotein signal sequence, Bacillus cereus penicillinase III signal sequence, and S. aureus penicillinase signal sequence, said facilitating region comprising a tetrapeptide selected from the group consisting of leu-ala-gly-cys and leu-serala-cys, said facilitating region having a single cysteine, the presence of which is necessary for the formation of a membrane bound lipoprotein wherein the modification to said exo-signal peptide comprises another amino acid X in place of said cysteine of the facilitating region, said amino acid X not forming a membrane bound lipoprotein but forming substantially more exoprotein that said wild-type signal peptide sequence.

12. A replicable expression vector effective in pyrocaryotic recombinant host cells in expressing a DNA sequence encoding an exo-signal peptide which comprises an amino acid sequence Met-Lys-Leu-Trp-Phe-Ser-Thr-Leu-Lys-Leu-Lys-Lys-Ala-Ala-Ala-Val-Leu-LeuPhe-Ser-Cys-Val-Ala-Leu-Ala-Gly-X-Y-(Asn-Asn-Gln-Thr-Asn-Ala)$_n$ wherein X is serine or alanine, Y is alanine or proline, and n is 0 or 1.

13. Recombinant host cells transformed with the vector of claim 12.